US011432830B2

(12) United States Patent
Bosworth

(10) Patent No.: US 11,432,830 B2
(45) Date of Patent: Sep. 6, 2022

(54) SECURING A BONE GRAFT TO THE GLENOID BONE AND IMPLEMENTATIONS THEREOF

(71) Applicant: Conmed Corporation, Utica, NY (US)

(72) Inventor: Adrian Bosworth, Bradenton, FL (US)

(73) Assignee: Conmed Corporation, Utica, NY (US)

( * ) Notice: Subject to any disclaimer, the term of this patent is extended or adjusted under 35 U.S.C. 154(b) by 274 days.

(21) Appl. No.: 16/765,045

(22) PCT Filed: Nov. 14, 2018

(86) PCT No.: PCT/US2018/060930
§ 371 (c)(1),
(2) Date: May 18, 2020

(87) PCT Pub. No.: WO2019/099451
PCT Pub. Date: May 23, 2019

(65) Prior Publication Data
US 2020/0405326 A1 Dec. 31, 2020

Related U.S. Application Data

(60) Provisional application No. 62/585,968, filed on Nov. 14, 2017.

(51) Int. Cl.
A61B 17/58 (2006.01)
A61B 17/60 (2006.01)
(Continued)

(52) U.S. Cl.
CPC ...... A61B 17/1684 (2013.01); A61B 17/1635 (2013.01); A61B 17/683 (2013.01);
(Continued)

(58) Field of Classification Search
CPC combination set(s) only.
See application file for complete search history.

(56) References Cited

U.S. PATENT DOCUMENTS 8,864,834 B2 10/2014 Boileau et al.
8,926,661 B2 1/2015 Sikora et al.
(Continued)

FOREIGN PATENT DOCUMENTS

WO 2016/145152 9/2016

OTHER PUBLICATIONS

Taverna, E. et al., 'Arthroscopically assisted Latarjet procedure: A new surgical approach for accurate coracoid graft placement and compression', International Journal of Shoulder Surgery, 2013, vol. 7, Issue 3, pp. 120-123.
(Continued)

Primary Examiner — Sameh R Boles
(74) Attorney, Agent, or Firm — Bond, Schoeneck & King, PLLC; Frederick J. M. Price

(57) ABSTRACT

A method of securing a bone graft to an anterior surface of a patient's glenoid bone, including drilling first and second bores through a posterior surface to an anterior surface of the glenoid bone; measuring a medial distance of the first bore; transferring the medial distance to a bone block; drilling a third bore based on the medial distance through the bone block to match the first bore; positioning the bone block in contacting relation with the anterior surface of the glenoid bone, and coaxially lining up the third bore with the first bore; positioning a first fastener through the third bore and the first bore; drilling a fourth bore in the bone block by positioning a drill bit through the second bore from the posterior side of the glenoid bone, and extending the drill bit from the first surface of the bone block to the second surface of the bone block; and positioning a second fastener through the fourth bore and the second bore.

19 Claims, 30 Drawing Sheets

(51) Int. Cl.
  *A61F 2/00* (2006.01)
  *A61B 17/16* (2006.01)
  *A61B 90/00* (2016.01)
  *A61B 17/68* (2006.01)
  *A61B 17/84* (2006.01)
  *A61B 17/88* (2006.01)

(52) U.S. Cl.
  CPC ........ *A61B 17/842* (2013.01); *A61B 17/8861* (2013.01); *A61B 90/06* (2016.02); *A61B 2090/061* (2016.02)

(56) References Cited

U.S. PATENT DOCUMENTS

| | | |
|---|---|---|
| 8,974,536 B2 | 3/2015 | Walch et al. |
| 9,089,435 B2 | 7/2015 | Walch et al. |
| 9,320,557 B2 | 4/2016 | Wyman et al. |
| 9,351,844 B2 | 5/2016 | Walch et al. |
| 9,636,102 B2 | 5/2017 | Sikora et al. |
| 9,877,736 B2 | 1/2018 | Wyman et al. |
| 10,123,813 B2 | 11/2018 | Boileau et al. |
| 10,172,627 B2 | 1/2019 | Haberman et al. |
| 2017/0112625 A1 | 4/2017 | Taverna et al. |
| 2019/0307568 A1* | 10/2019 | Bettenga .............. A61B 17/683 |

OTHER PUBLICATIONS

AU Exam Report No. 1, App. No. 2018369746, dated Feb. 5, 2021, pp. 1-10.

E. Taverna, et al., Arthroscopic Bone Graft Procedure for Anterior Inferior Glenohumeral Instability, 2015 Arthroscopy Association of North America 2212-6287/14524, thelancet.com.

JP Office action, App. No. 2020-544384, dated May 11, 2021, pp. 1-8.

* cited by examiner

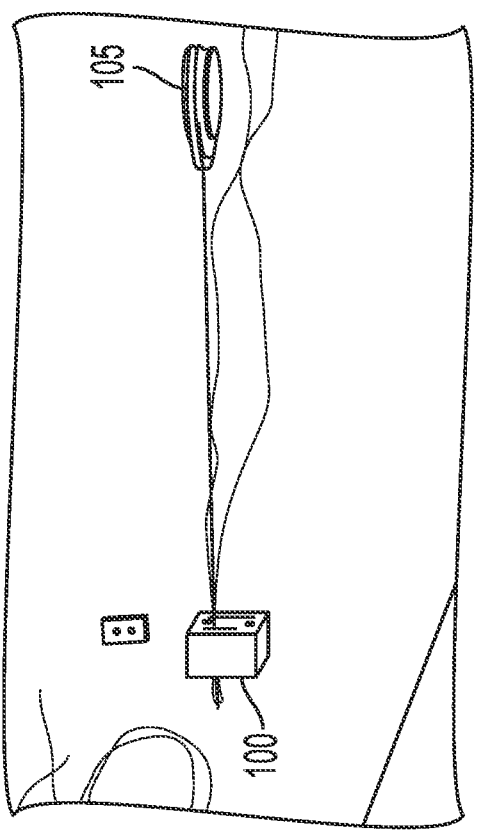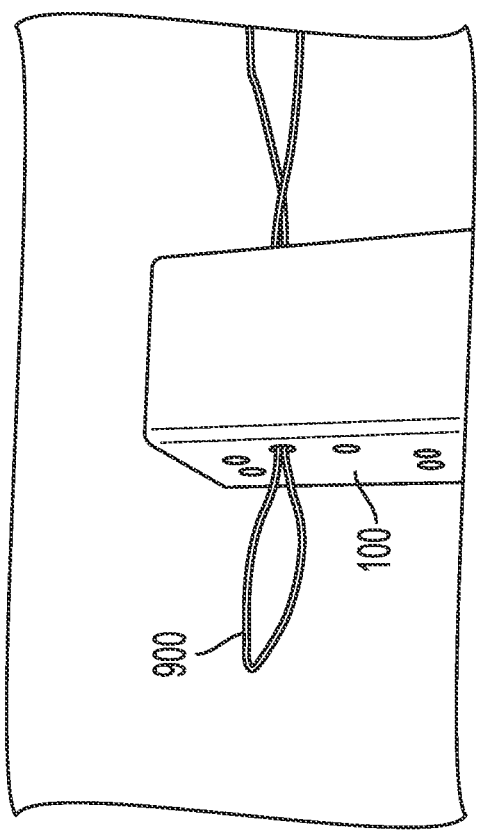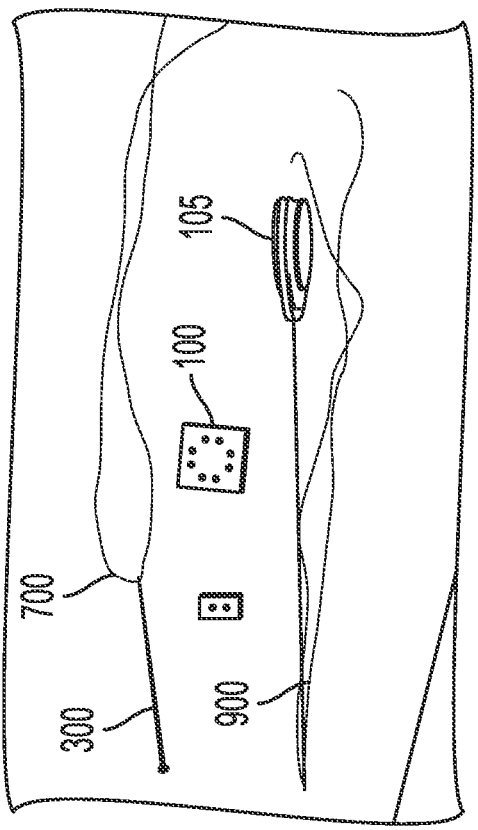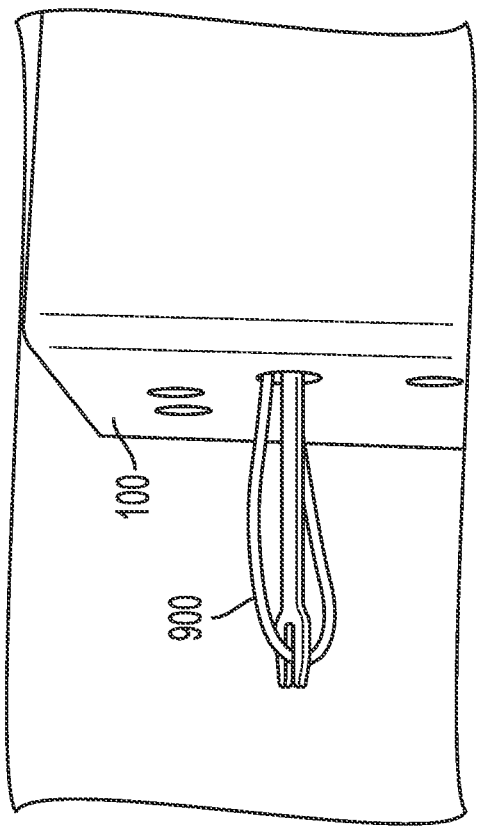

SECURING A BONE GRAFT TO THE GLENOID BONE AND IMPLEMENTATIONS THEREOF

CROSS-REFERENCES TO RELATED APPLICATIONS

This application is a national stage application under 35 U.S.C. 371 based on international patent application PCT/US18/60930 filed on Nov. 14, 2018, which claims priority to U.S. Provisional Patent Application Ser. No. 62/585,968, filed on Nov. 14, 2017.

BACKGROUND OF THE INVENTION

1. Field of the Invention

The present disclosure is directed generally to surgical devices and surgical procedures for securing a bone graft, and more particularly, to a surgical device for securing a bone graft to the glenoid bone from the posterior side of the body to treat recurrent shoulder instability.

2. Description of the Related Art

One common cause of chronic shoulder pain and shoulder instability is recurrent shoulder dislocation. When a shoulder becomes dislocated, it causes trauma to the surrounding tissues and bones. Specifically, shoulder dislocation causes deterioration of the glenoid bone. As the glenoid bone is worn down, it begins to lose its ability to stabilize the shoulder. Thus, recurrent shoulder dislocations cause a glenoid bone deficiency, which in turn, makes the shoulder more susceptible to subsequent dislocations.

There are many conventional surgical procedures for treating shoulder instability. One such surgical technique includes soft tissue repair. This may include the tightening of ligaments, such as those connecting the glenoid to the humerus. However, repair of the ligaments in the shoulder may not be sufficient to prevent recurrent shoulder dislocations when there is a glenoid bone deficiency. Relying on tissue to prevent dislocation can cause the tissue to stretch from overuse, which will ultimately lead to subsequent dislocations and trauma. Other surgical procedures require the implantation of a shoulder prosthesis. However, shoulder replacement surgery is often recommended only in more severe circumstances, such as when cartilage is lost as a result of arthritis or when components of the shoulder have been severely fractured.

There are surgical procedures to treat an intermediate level of shoulder instability. Some of the techniques require securing a coracoid bone autograft against the glenoid bone surface which necessitates the release of the coracoacromial ligament (CAL) when harvesting the coracoid. There are several studies affirming that detachment of the CAL increases the magnitude of superior humeral translation of the shoulder. These techniques must be performed through anterior incisions in the body which are in close proximity to fragile nerves and blood vessels. These types of procedures also require an incision through the subscapularis, the largest of the four tendomuscular structures in the rotator cuff group, for the insertion of the bone graft.

Additionally, many bone graft techniques to treat shoulder instability require screws to secure the bone graft against the glenoid bone. The screws may also cause excess trauma and strain on the glenoid bone. Accordingly, there is a need in the art for a surgical apparatus and method to secure a bone graft to the glenoid bone which causes less trauma to the glenoid bone and surrounding soft tissue with lower risk of damage to nerves and blood vessels.

Description of the Related Art Section Disclaimer: To the extent that specific patents/publications/products are discussed above in this Description of the Related Art Section or elsewhere in this Application, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

Embodiments of the present invention recognize that there are potential problems and/or disadvantages with the conventional devices and methods for securing a bone graft to the glenoid bone as described above. Therefore, a need exists for a simplified and alternative approach to secure a bone graft or artificial implant to the glenoid bone to reduce anterior shoulder instability which effects less trauma to the glenoid bone and surrounding soft tissue and greatly reduces risk of damage to nearby nerves and blood vessels. Various embodiments of the present invention may be advantageous in that they may solve or reduce one or more of the potential problems and/or disadvantages discussed herein.

The anterior glenoid defect may typically consist of 20% to 30% of bone loss through erosion due to frequent shoulder dislocations. As discussed and illustrated in the detailed description herein and below, in accordance with one embodiment, an arthroscopic glenoid augmentation surgical procedure is provided. In brief, as a first step, the damaged area can be resected by using a reciprocating rasp to produce a flat surface to accept the graft and expose fresh cancellous bone in order to promote healing. After the creation of the standard arthroscopic visualization and access portals, with the exception of the posterior portal which can be created more superior and closer to the acromion, a hooked beam of a trans-glenoid drill guide can be introduced through a small incision from posterior to anterior and its hooked end located against the previously resected anterior surface of the glenoid. The hooked beam can incorporate a flat on its underside which may be used to visualize the correct rotational alignment of the drill guide to the articular surface of the glenoid. Upon achieving the desired trajectory of the drill guide, the drill guide tubes are introduced arthroscopically through two small incisions and inserted through the soft tissue until they make contact with the posterior surface of the glenoid neck. Each of the drill guide tubes may be independently released to slide freely or independently locked by depressing or releasing its lever. Another embodiment of the design could incorporate a single lever to simultaneously actuate both locking mechanisms. See U.S. Pat. No. 5,154,720 for an example of a collet locking mechanism for ACL guide, which can be used here. The drill guide can be secured to the glenoid by applying light pressure to the ends of the tubes and releasing the locking levers.

Both glenoid tunnels can then be drilled via drill guide tubes and both drills can be left temporarily in place to increase stability. The hooked beam of the drill guide can then be detached and withdrawn a small distance posteriorly. Due to the less favorable visualization of the anteroinferior glenoid area when compared with its anterosuperior, it may be desirable to insert the inferior implant first. It may also be favorable to use a shorter drill for the first hole and a longer drill for the second hole. This technique would be beneficial when drilling the second hole as it could prevent the drill chuck or pin driver head from fouling on the proximal end of the first drill, as would be the case if both drills used were of equal length. Also employing the method of drilling the inferior hole second could obviate a need to swap the chuck or pin driver back and forth since the inferior drill would be the first drill to be removed prior to the next step of inserting the inferior implant.

After each hole has been drilled as described above, an expanding cannula attached to a special inserter can be inserted through the rotator cuff interval and into the capsule. The inserter is removed and the expanding cannula deployed. The expanding cannula may consist of a roll of plastic film inside a tube. Also it may consist of third piece such as a shaft inside the tube to assist insertion and deployment of the roll of plastic film. The inferior drill can then be removed. A suture passer or a Y-Knot® inserter shaft (see, e.g., U.S. Pat. No. 9,173,652) loaded with a looped suture can be inserted posteriorly through the glenoid and retrieved through the expanding cannula previously inserted into the rotator cuff interval portal. The suture tails of a peek implant are threaded through the previously drilled inferior hole of the bone block graft. The peek implant may consist of a zip tie with an integrally molded peek cylinder with a head larger than the cylindrical shaft. The implant may have a passing suture attached to one end in order for it to be drawn through the graft and glenoid and out through the drill guide tubes. After the primary implant suture tails have been drawn through the inferior drill guide tube, the bone block graft is shuttled down the suture, through the expanding cannula and into the capsule. The graft is positioned against the resected surface and the peek implant is drawn through the graft and glenoid. The graft is now free to rotate about the axis of the first implant's cylindrical section until it is aligned with the articular surface of the glenoid. The hooked beam tip of the drill guide is then advanced over the graft and the drill guide reattached to secure the graft.

The drill chuck or pin driver is reattached to proximal end of the second drill bit and the existing glenoid tunnel is extended out through the anterior surface of the bone block graft. The second implant is inserted using the same process as previously described and the drill guide and expanding cannula removed. Peek locking buttons, for example, are threaded onto the ends of the zip tie portion of the implants which extend out the posterior dermis. The locking buttons are then slid distally down the zip ties until they make contact the posterior glenoid neck. A tensioning device is then attached to the zip tie and a predetermined force applied between the locking button and implant to set the implants with the desired tension. The tensioning device can consist of some gripping jaws to hold the proximal end of the zip tie and a mechanism capable of applying a tensile force to the gripping jaws relative to the locking button. Some indicator of the magnitude of force being applied can also be used. A zip tie cutting device is then slid down the zip tie and actuated in order to cut the excess zip tie off flush with the proximal surface of the locking button. The device may have a rotary cutting action whereby the zip tie strap passes through a slot in the device's tip and an internal blade rotates against that slot to cut the zip tie.

The present disclosure is also directed to an inventive configuration, structure, and resulting function of an apparatus for improving shoulder instability. Various embodiments herein are directed to an apparatus for improving shoulder instability, including, but not limited to: an apparatus for improving shoulder stability, comprising: a bone block having a first surface and a second surface; wherein the second surface of the bone block is disposed on a first side of a boney member; a bore extending through both the bone block and the boney member; a fastener having a cord with a free end and a button affixed to an opposing end with a ratcheted section therebetween; wherein the cord extends through the bore such that the button rests on the first surface of the bone block and the free end extends through a second side of the boney member; a tensioning lock configured to slide from a free end of the cord towards the button; wherein in a locked position, the tensioning lock is affixed to the ratcheted section.

According to an alternative embodiment, a method for grafting a bone block onto a glenoid bone, includes, but is not limited to the steps of: providing a bone block having a first surface and a second surface, wherein the second surface of the bone block is disposed on a first side of a glenoid bone, a bore extending through both the bone block and the glenoid bone, a fastener having a cord with a free end and a button affixed to an opposing end with a ratcheted section therebetween, and a tensioning lock configured to slide from a free end of the cord towards the button; pulling the cord through the bore until the button rests on the first surface of the bone block and the free end of the cord extends from the second side of the glenoid bone; sliding the tensioning lock onto the free end of the cord towards the second side of the glenoid bone; and securing the tensioning lock along the cord at the ratcheted section.

According to an another aspect, a method for grafting a bone block onto a glenoid bone, includes, but is not limited to the steps of: drilling a first bore and a second bore through a glenoid bone; drilling a third bore through a bone block; securing a fastener having a cord with a free end and a button affixed to an opposing end with a ratcheted section therebetween to the third bore with an implant suture; injecting a tube into a rotator cuff interval; depositing the bone block secured to the fastener by the implant suture into the rotator cuff interval; and pulling the implant suture through the first bore until the button of the fastener rests on the bone block and the free end of the cord extends through the first bore.

The details of one or more embodiments are described below and in the accompanying drawings. Other objects and advantages of the present invention will be apparent from and elucidated with reference to the embodiment(s) described hereinafter.

BRIEF DESCRIPTION OF THE DRAWINGS

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which:

FIG. 6A is a picture showing part of a method showing passing a suture through a bone block with a suture passer of an embodiment;

FIG. 6B is a picture showing part of a method showing passing a suture 900 through a bone block with a suture passer of an embodiment;

FIG. 6C is a picture showing part of a method showing passing a suture 900 through a bone block with a suture passer of an embodiment;

FIG. 6D is a picture showing part of a method showing passing a suture 900 through a bone block with a suture passer of an embodiment;

Figure 1A:
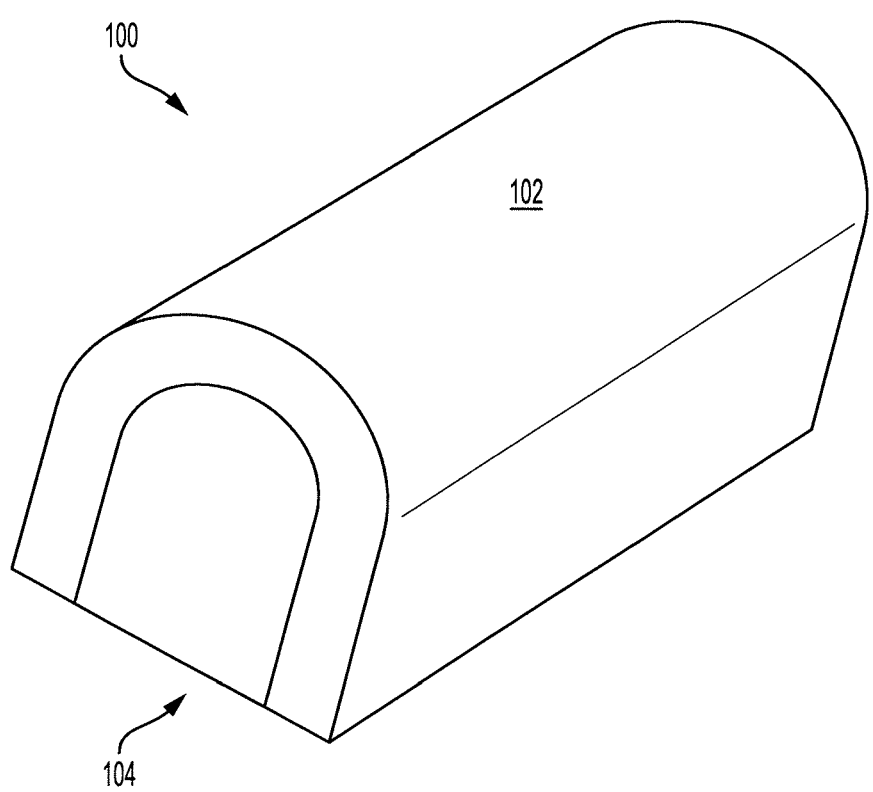
FIG. 1A is a perspective view schematic representation of an exemplary embodiment of a bone block.

Where applicable, like reference characters designate identical or corresponding components and units throughout the several views, which are not to scale unless otherwise indicated. Moreover, the embodiments disclosed herein may include elements that appear in one or more of the several views or in combinations of the several views.

DETAILED DESCRIPTION

Aspects of the present invention and certain features, advantages, and details thereof, are explained more fully below with reference to the non-limiting examples illustrated in the accompanying drawings. Descriptions of well-known structures are omitted so as not to unnecessarily obscure the invention in detail. It should be understood, however, that the detailed description and the specific non-limiting examples, while indicating aspects of the invention, are given by way of illustration only, and are not by way of limitation. Various substitutions, modifications, additions, and/or arrangements, within the spirit and/or scope of the underlying inventive concepts will be apparent to those skilled in the art from this disclosure.

Referring now to the drawings, wherein like reference numerals refer to like parts throughout, there is seen in FIG. 1A a perspective view schematic representation of an exemplary embodiment of a bone block 100 for implantation into the shoulder. The bone block 100 is part of a surgical graft system that also includes a fastener 300, shown in FIG. 1B. Referring back to FIG. 1 A, the bone block 100 can be an autograft, an allograft, or an artificial and biocompatible implant (as should be understood by those of ordinary skill in the art in conjunction with a review of this disclosure). In one embodiment, the bone block 100 is harvested from the pelvic iliac crest. The bone block 100 in the depicted embodiment is shaped such that it has a rounded anterior side 102 and a flat posterior side 104, and can generally fit and be sized and positioned (as should be understood by those of ordinary skill in the art in conjunction with a review of this disclosure) at the glenoid bone. When the bone block 100 is implanted, the posterior side 104 is in contact with the glenoid bone; therefore, the posterior side 104 is flat to facilitate a substantially to fully flush connection between the bone block 100 and the glenoid bone.

Figure 1B:
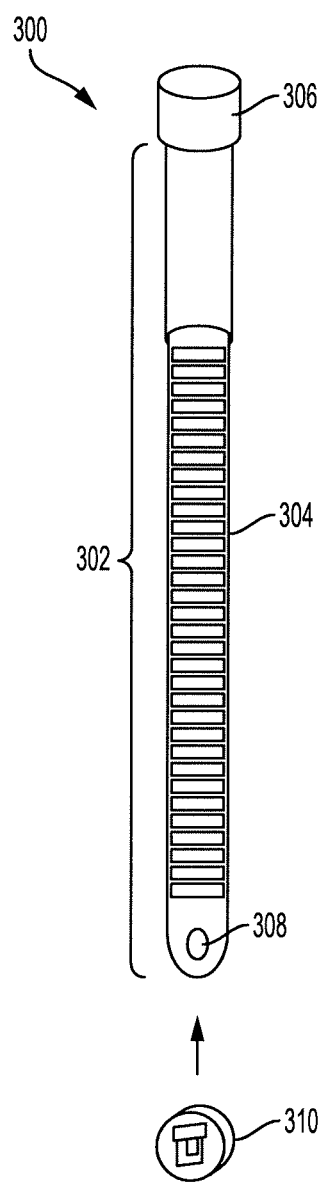
FIG. 1B is a perspective view schematic representation of an exemplary embodiment of a fastener of an embodiment.
Figure 22A:
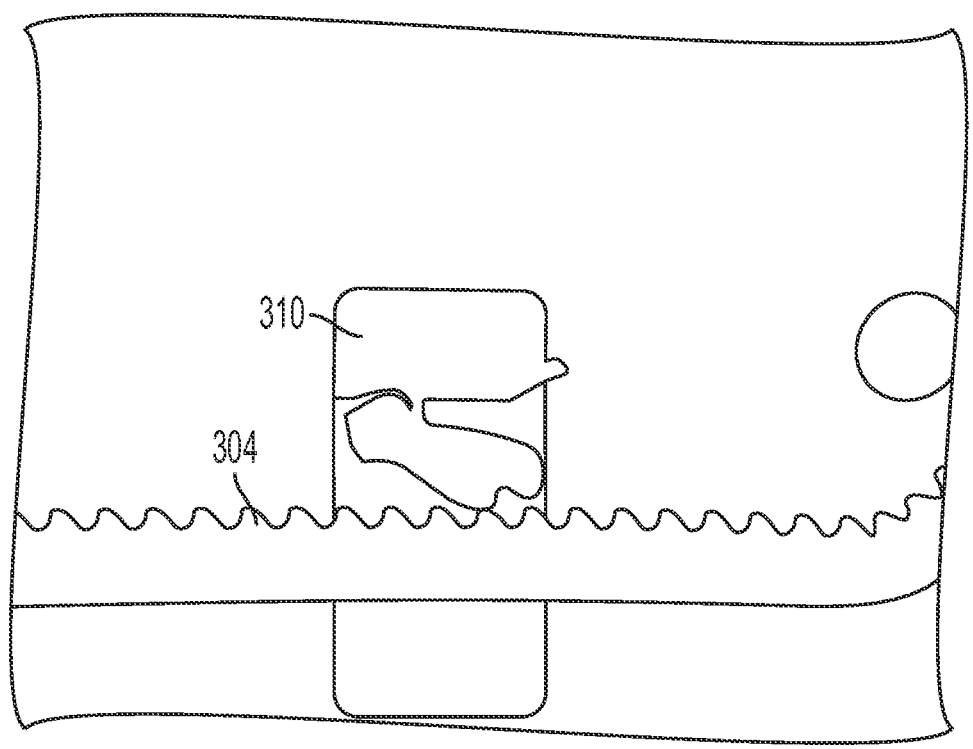
FIG. 22A is a picture showing a sectioned view of a tensioning lock positioned between grooves between teeth of a ratcheted section of a fastener of an embodiment.
Figure 22B:
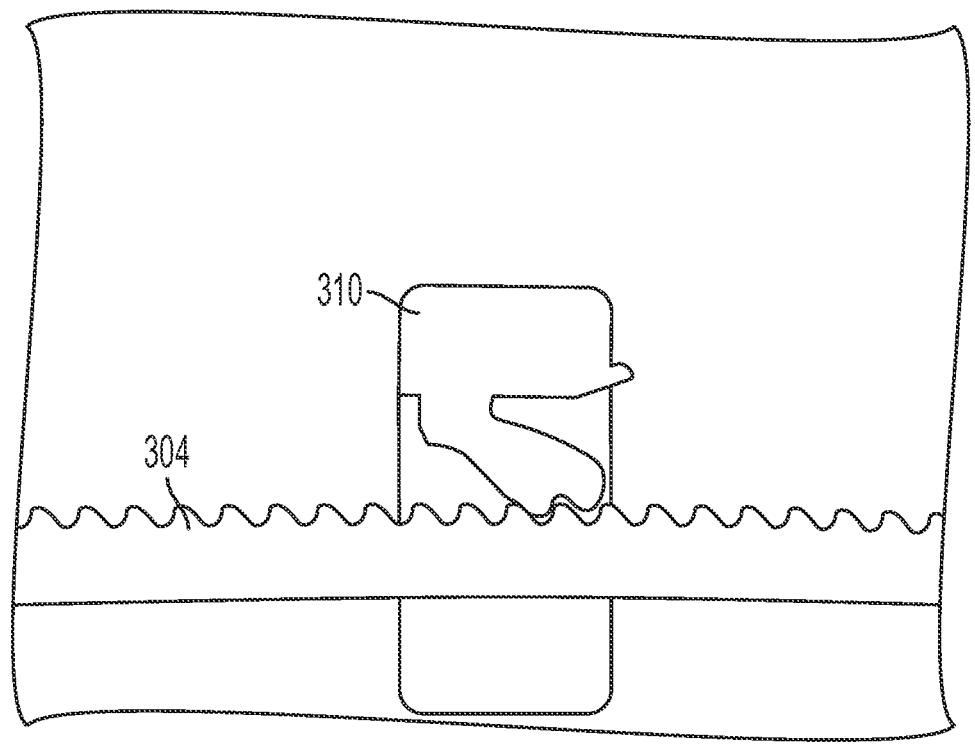
FIG. 22B is a picture showing a sectioned view of a tensioning lock positioned in a groove between teeth of a ratcheted section of a fastener of an embodiment.

Referring now to FIG. 1B, there is shown a perspective view schematic representation of an exemplary embodiment of the fastener 300 for implanting the bone block 100 on the glenoid bone. The fastener 300 comprises a cord 302 having a ratcheted section 304. In the depicted embodiment, the ratcheted section 304 comprises a majority of the cord 302; however, in other embodiments, the ratcheted section 304 comprises less than a majority of the cord 302. The fastener 300 further comprises a button head 306 affixed to one end of the cord 302, which can have (but does not have to) a larger area than the rest of the cord 302. The opposing free end of the cord 302 comprises an aperture 308 configured to receive suture material. An example of fastener 300 can be a zip tie (made from, e.g., any biocompatible material such as PEEK and/or PEG material), as should be understood by those of ordinary skill in the art in conjunction with a review of this disclosure. The zip tie embodiment is discussed further herein below, and its functionality and partial structure is illustrated in FIG. 22A-B showing a sectioned view of tensioning lock 310 positioned between grooves between teeth (FIG. 22A) of a ratcheted section 304 of fastener 300, and positioned in a groove between teeth (FIG. 22B) of a ratcheted section 304 of fastener 300.

Referring still to FIG. 1B, the free end of the cord 302 is adapted to receive a tensioning lock 310. In use, the free end of the cord 302 is fed through the tensioning lock 310. Features of the tensioning lock 310 hook to the ratcheted section 304 and prevent the tensioning lock 310 from being pulled back towards the free end of the cord 302. Thus, the tensioning lock 310 can be progressed farther along the ratcheted section 304 towards the button 306, but cannot be pulled back in the opposite direction. Therefore, the tensioning lock 310 can efficiently lock an object on the cord 302 between the button 306 and the tensioning lock 310.

Figure 2A:
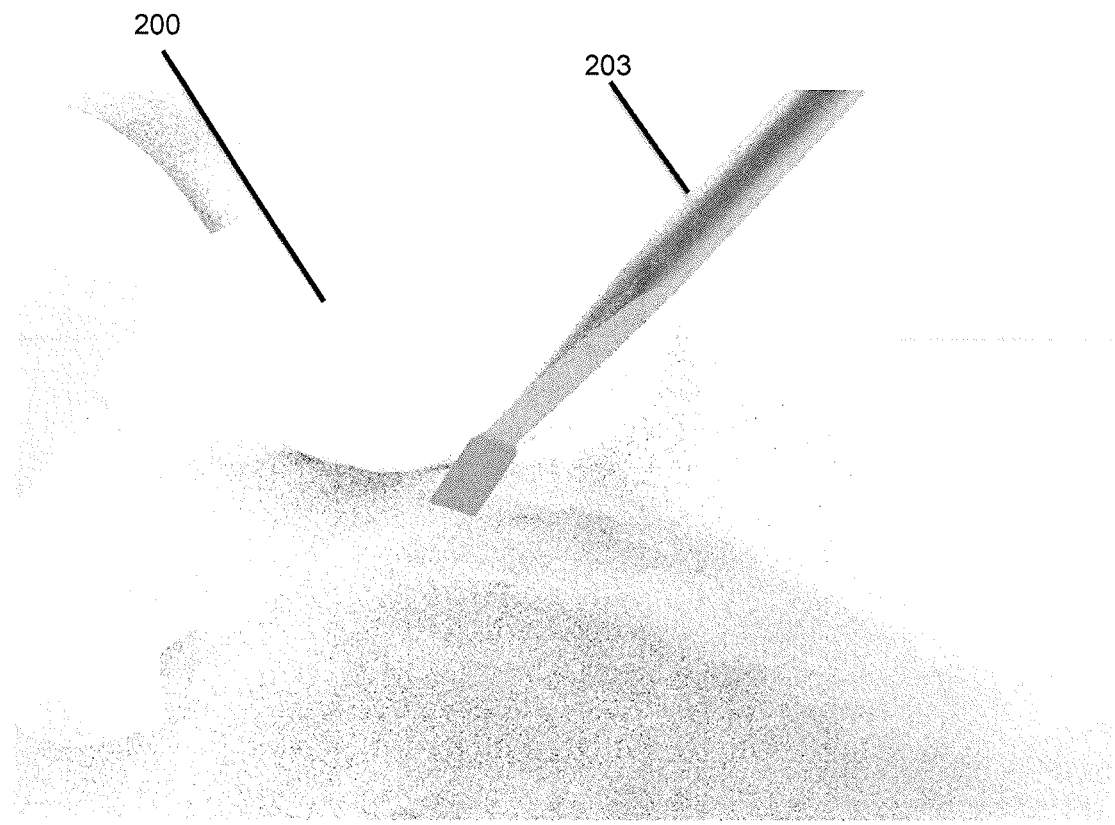
FIG. 2A is a perspective view schematic representation of an exemplary embodiment of a glenoid bone in preparation to receive the bone block.
Figure 2:
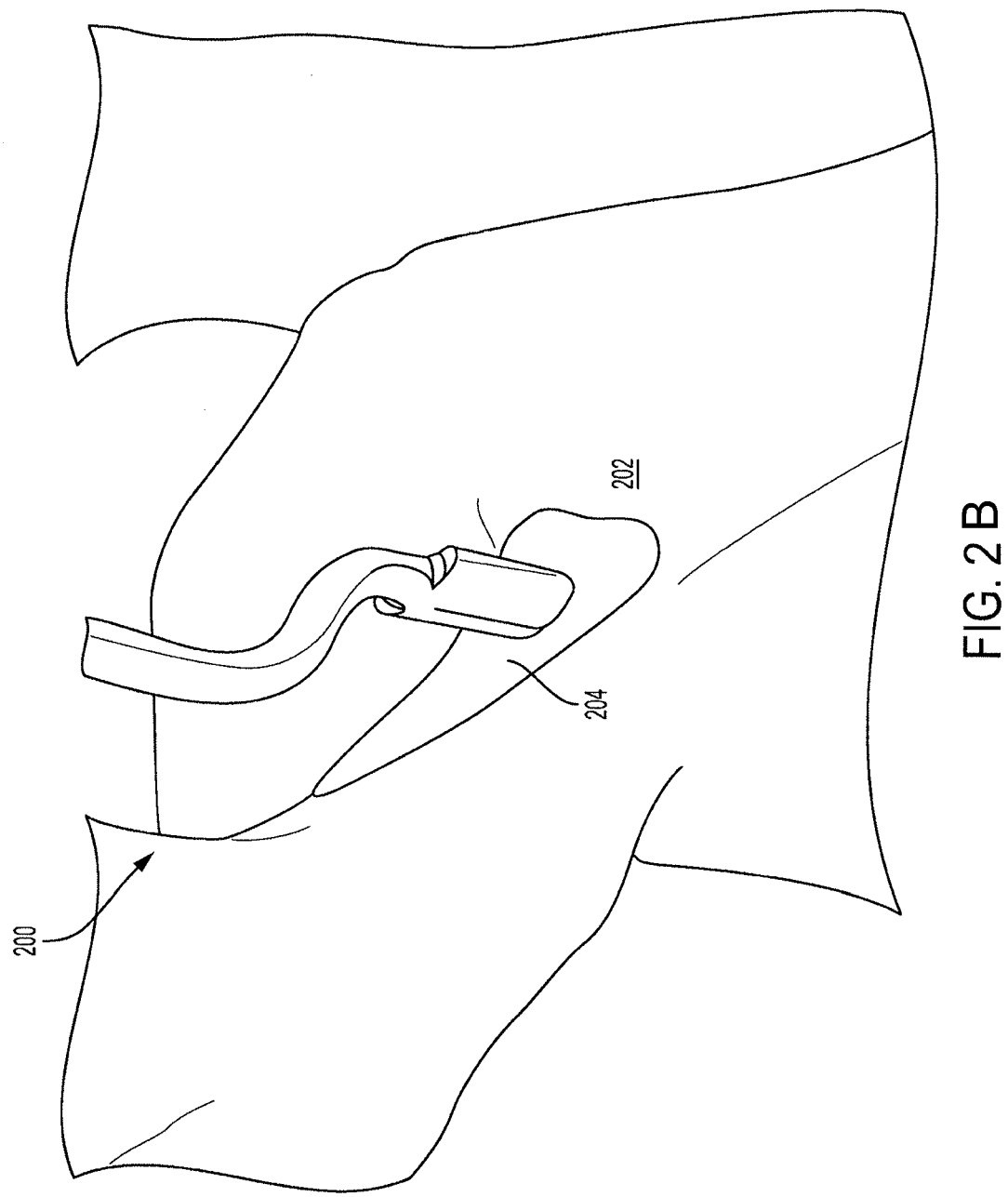
FIG. 2B is a perspective view schematic representation of an exemplary embodiment of a glenoid bone in preparation to receive the bone block.

Referring now to FIG. 2A-B, there are shown a perspective views of exemplary embodiments of a glenoid bone 200 in preparation to receive the bone block 100. Before the bone block 100 is implanted against the glenoid bone 200, the glenoid bone 200 is preferably prepared. Preparation may include removing soft tissue from the surface 202 of the glenoid bone 200. This may be accomplished with a tool such as a tissue elevator or liberator 203 (see FIG. 2A). The surface 202 can be further flattened with a reciprocating rasp 204 (see FIG. 2B). A smooth and flat area (e.g., squared off surface) on the glenoid bone 200 allows for better contact with the posterior side 104 of the bone block 100 in order to facilitate fusion of one to the other over time.

Figure 3:
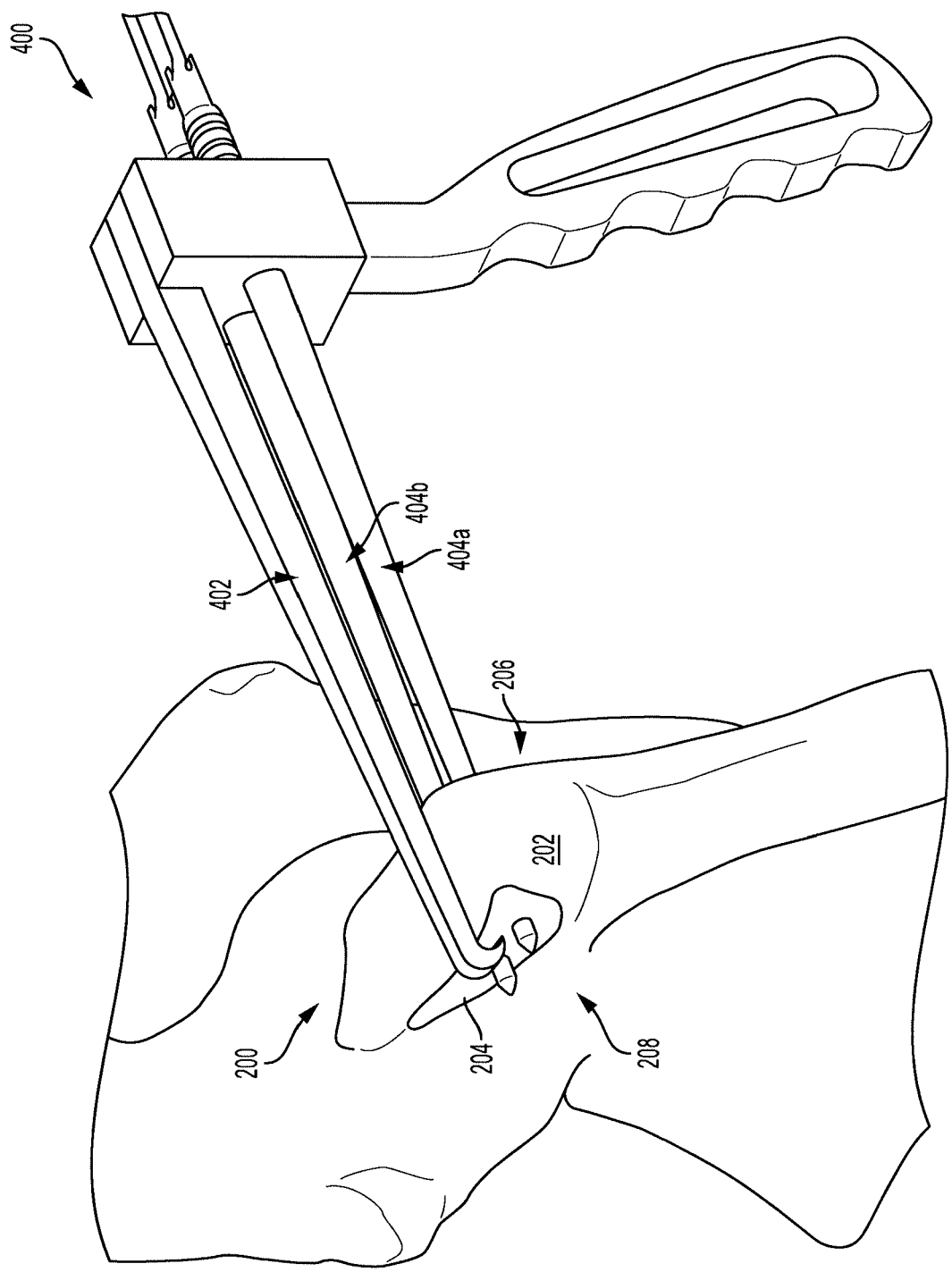
FIG. 3 is a perspective view schematic representation of an exemplary embodiment of a drill system attached to the glenoid bone through the posterior of the body of an embodiment.

Referring to FIG. 3, there is shown a perspective view exemplary embodiment of a drill system 400 attached to the glenoid bone 200. As the bone block 100 must be anchored to the glenoid bone 200 when it is implanted, both the bone block 100 and the glenoid bone 200 must be prepared to receive a fastener 300, such as that shown in FIG. 1B. In one embodiment, a drill system 400 enters the posterior side of the body and attaches to the glenoid bone 200. The drill system 400 in the depicted embodiment comprises a detachable clamping beam or hook 402 and two drill guides 404. The hook 402 is used to hold the glenoid bone 200 in place while drill bits within the drill guides 404 form bores the glenoid bone 200.

In the embodiment shown in FIG. 3, the drill system 400 is used to drill two bores through the glenoid bone 200. The two bores are drilled through the posterior side 206 of the glenoid bone. Drilling from the posterior is safer than drilling through the anterior of the body. When drilling from the posterior of the body, the drill avoids the nerves and blood vessels that may be damaged when drilling from the anterior of the body. Thus, drilling through the posterior side 206 of the glenoid bone 200 avoids additional trauma to the patient.

Figure 4:
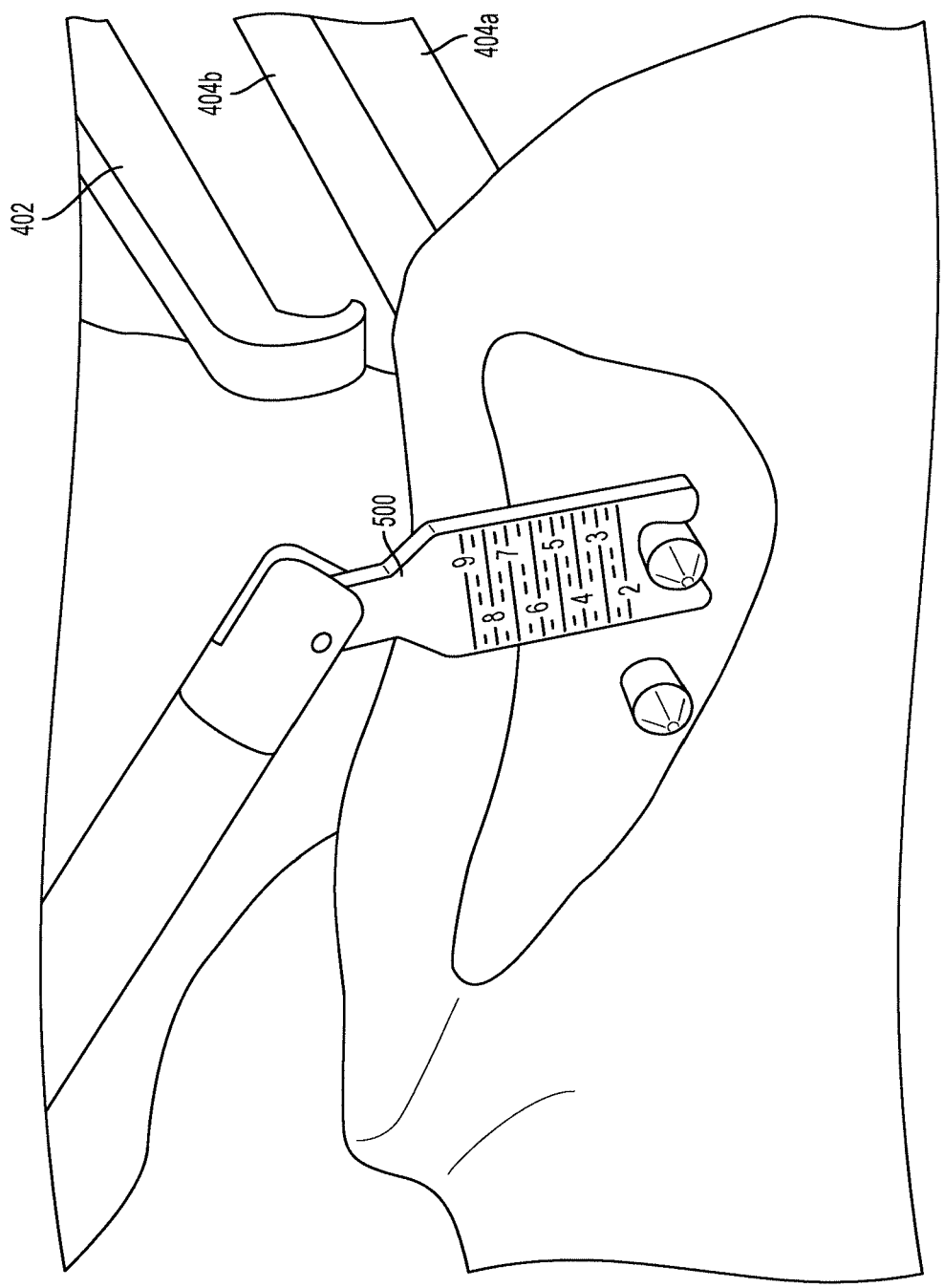
FIG. 4 is a perspective view schematic representation of an exemplary embodiment of a measuring device positioned on a drill bit of an embodiment.
Figure 5A:
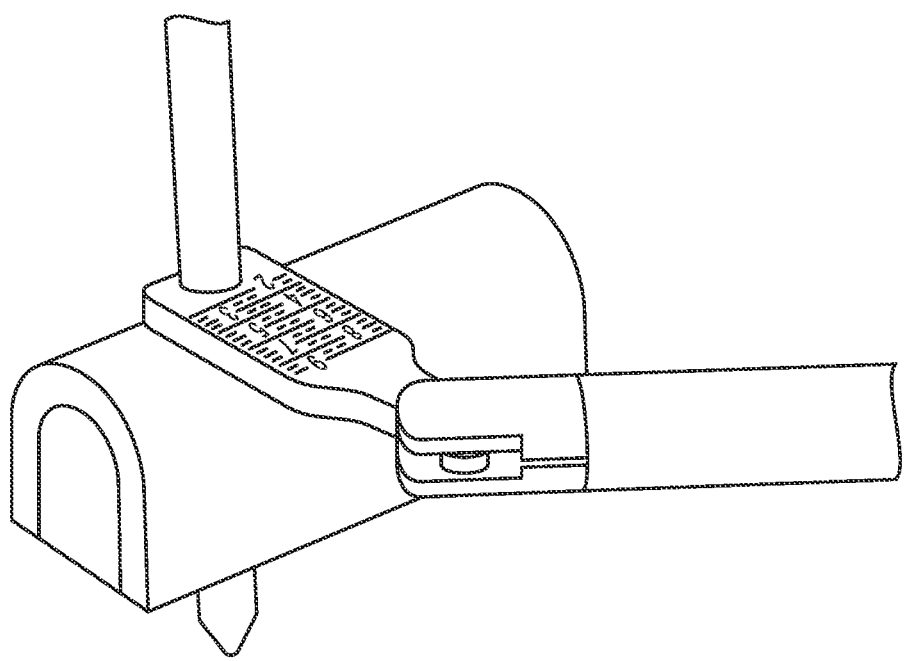
FIG. 5A is a perspective view schematic representation of an exemplary embodiment of a measuring device positioned on a bone block of an embodiment.
Figure 5B:
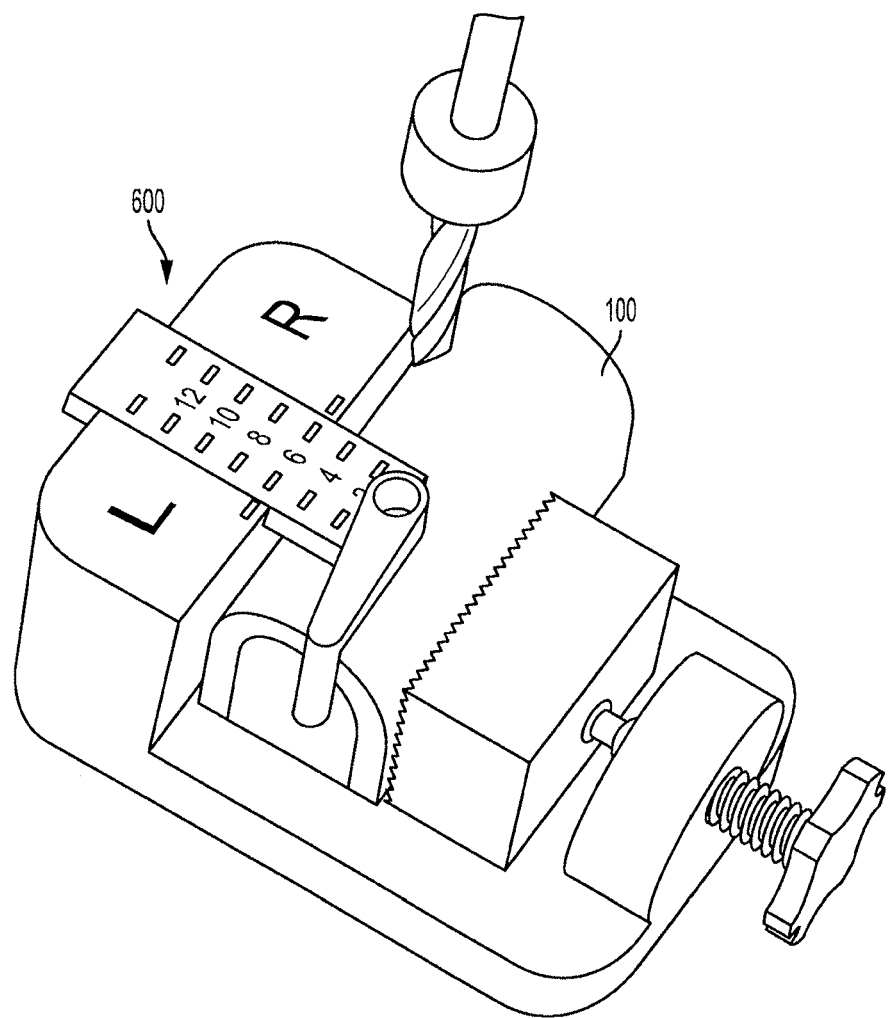
FIG. 5B is a perspective view schematic representation of an exemplary embodiment of a bone block clamped in a drilling jig with measuring indica of an embodiment.

Once the two bores are drilled through the glenoid bone 200, the drill guide hook 402 is removed (e.g., by pivoting and pulling posteriorly) and the drills and drill guides 404 are left in place. Then, referring now to FIG. 4, a measuring gauge device/paddle 500 is used to measure the medial distance of the inferior bore created by an inferior drill guide 404a. Referring to FIGS. 5A-B, the measurement obtained from the measuring device 500 in FIG. 4 can be transferred to the bone block 100 through use of a measuring gauge device/paddle 500 or on a drilling jig 600 with measuring indicia. Once the measurement is transferred, a single bore is drilled through the bone block 100 to match the inferior bore on the glenoid bone 200. After this step, the preparation of the bone block 100 and glenoid bone 200 is complete.

Figure 6:
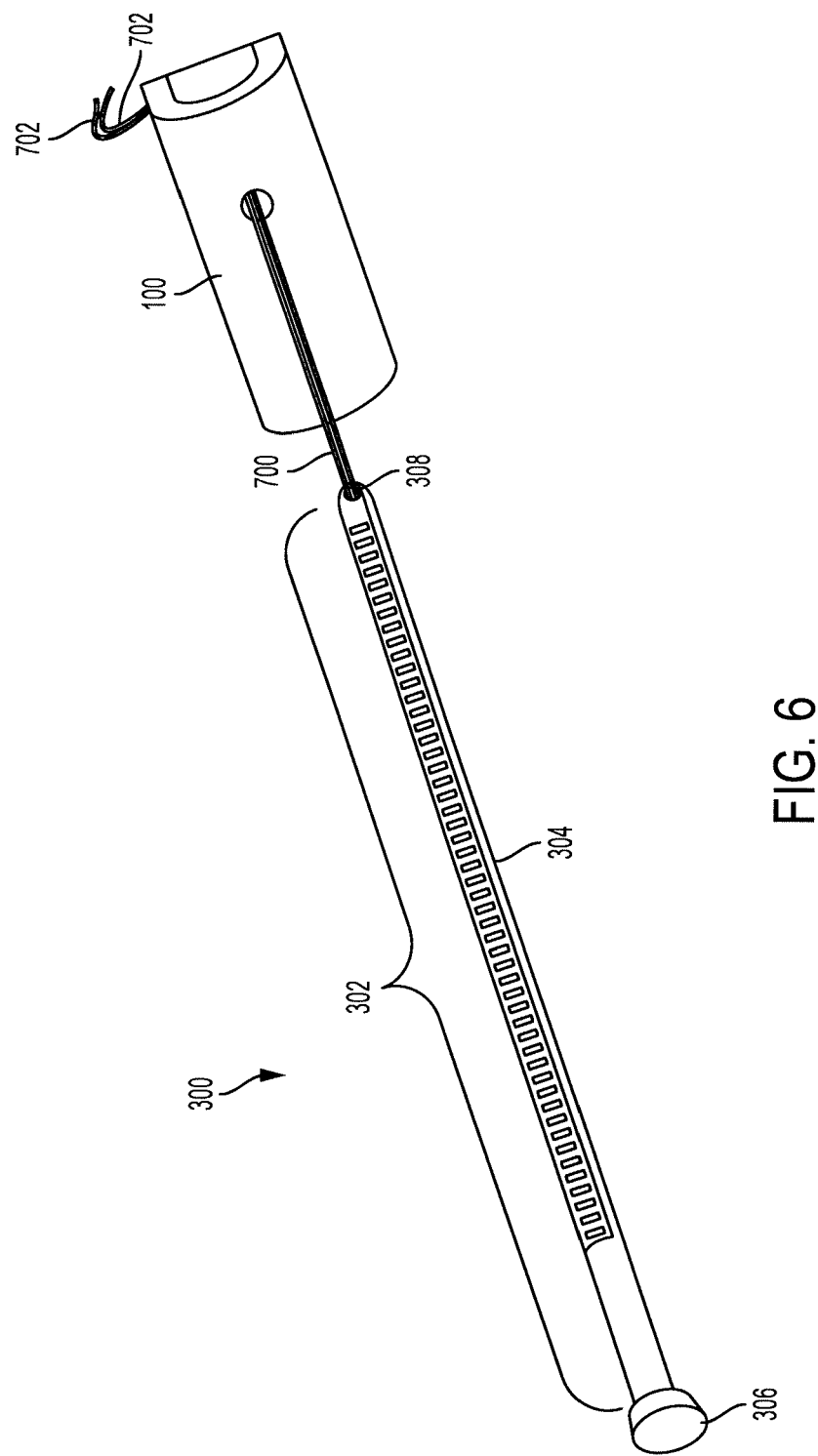
FIG. 6 is a perspective view schematic representation of an exemplary embodiment of an implant suture secured to the fastener of FIG. 1B and the bone block of FIG. 1A of an embodiment.
Figure 6F:
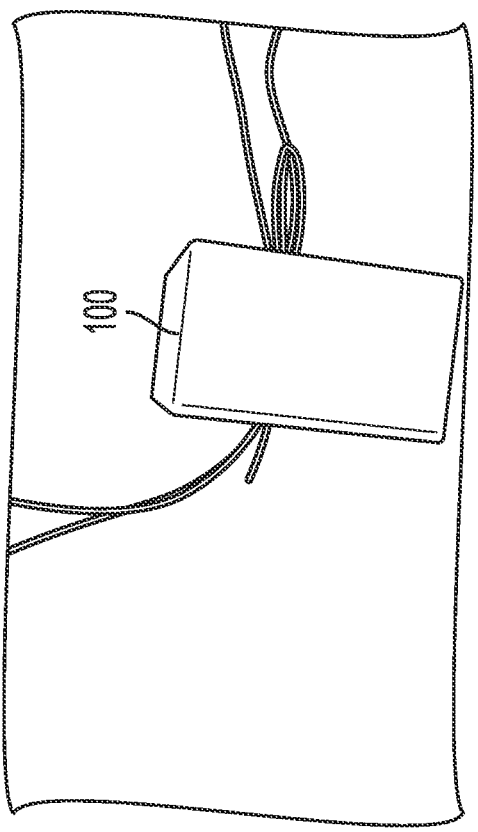
FIG. 6F is a picture showing part of a method showing successive steps of securing a bone block with fastener of an embodiment.
Figure 6H:
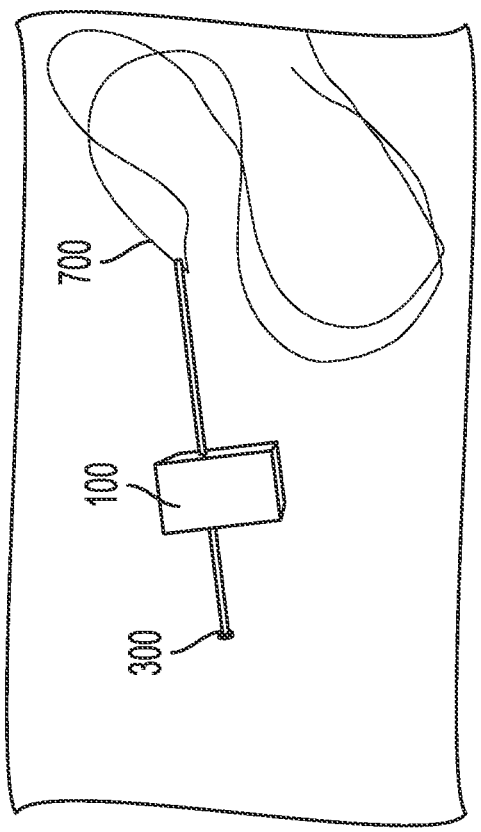
FIG. 6H is a picture showing part of a method showing successive steps of securing a bone block with fastener of an embodiment.
Figure 6E:
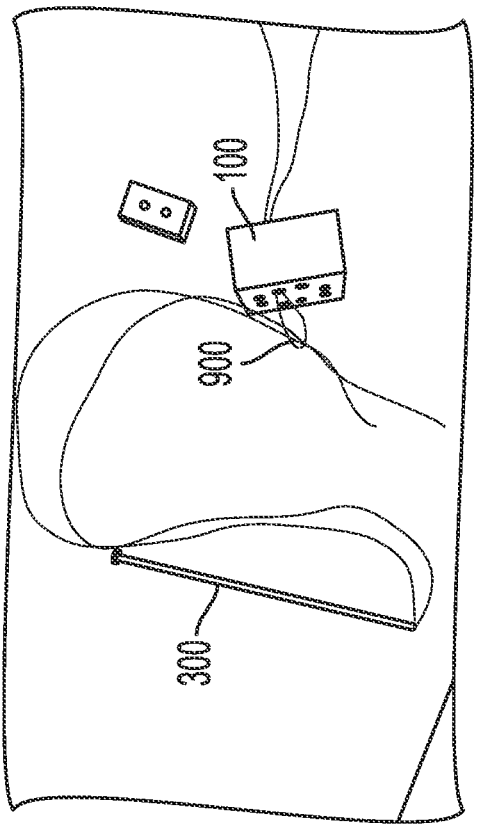
FIG. 6E is a picture showing part of a method showing successive steps of securing a bone block with fastener of an embodiment.
Figure 6G:
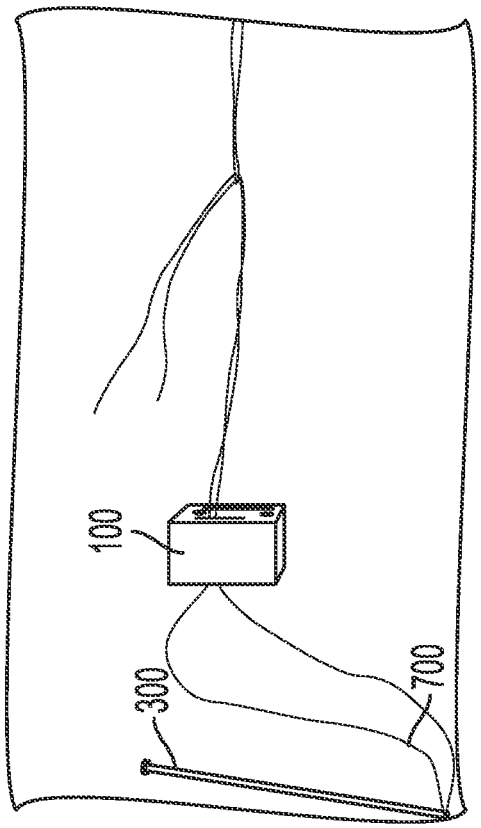
FIG. 6G is a picture showing part of a method showing successive steps of securing a bone block with fastener of an embodiment.

Referring now to FIG. 6, there is shown a perspective view exemplary embodiment of the bone block 100 threaded onto the fastener 300. In one embodiment, an implant suture 700a is used to connect the bone block 100 to the fastener 300. The implant suture is threaded through the aperture 308 at the free end of the fastener 300 and threaded through the bore on the bone block 100. The implant suture 700a can be secured to the fastener 300 and the bone block 100 according to conventional methods. However, in the depicted embodiment, the implant suture 700 is secured to the bone block 100 such that tails 702a of the implant suture 700a extend from the posterior side 104 of the bone block 100. See FIGS. 6A-D, showing successive steps of passing a suture 900 through a bone block with a suture passer, and FIGS. 6E-H showing successive steps of securing a bone block with fastener 300 (e.g., a zip tie).

Figure 7:
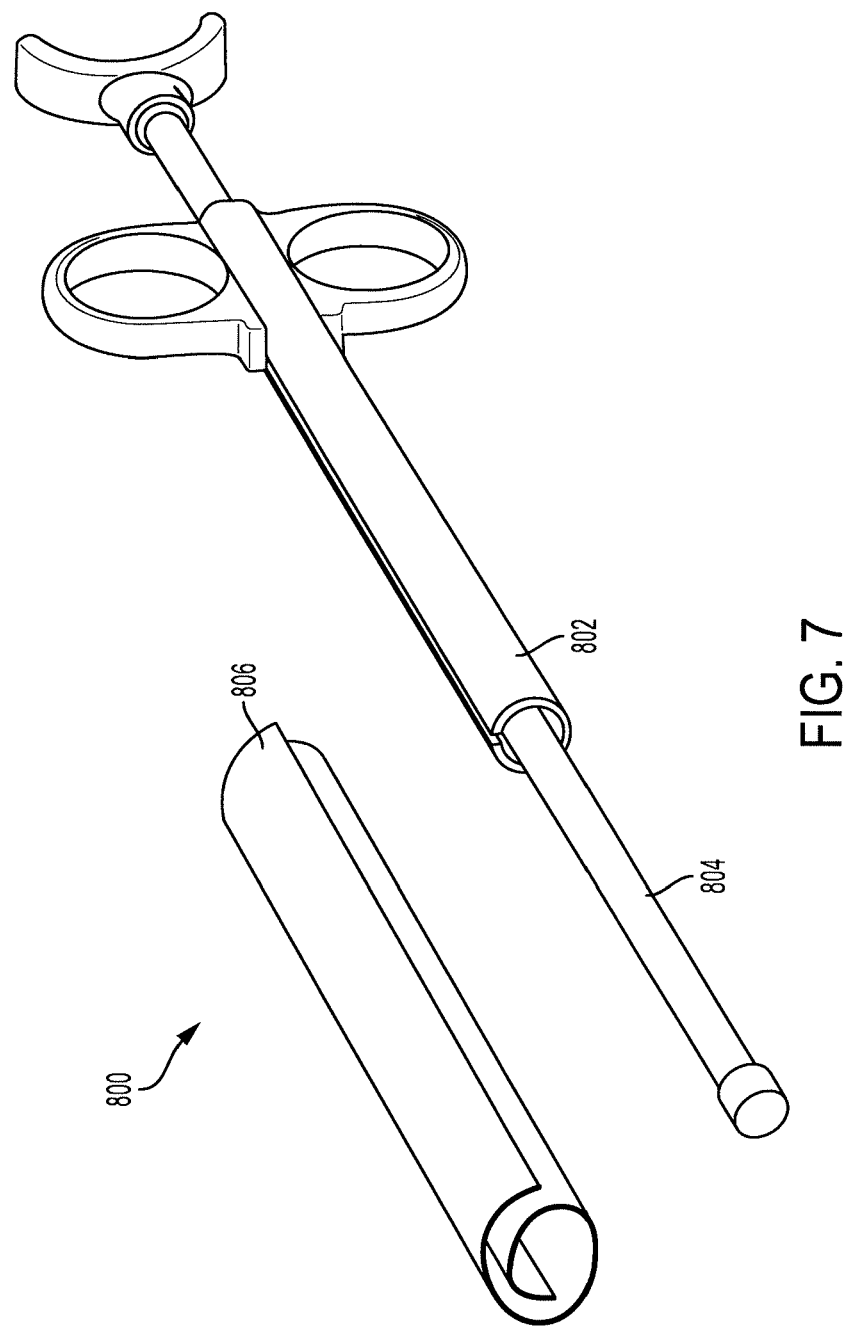
FIG. 7 is a perspective view schematic representation of an exemplary embodiment of an expanding cannula system; of an embodiment
Figure 8:
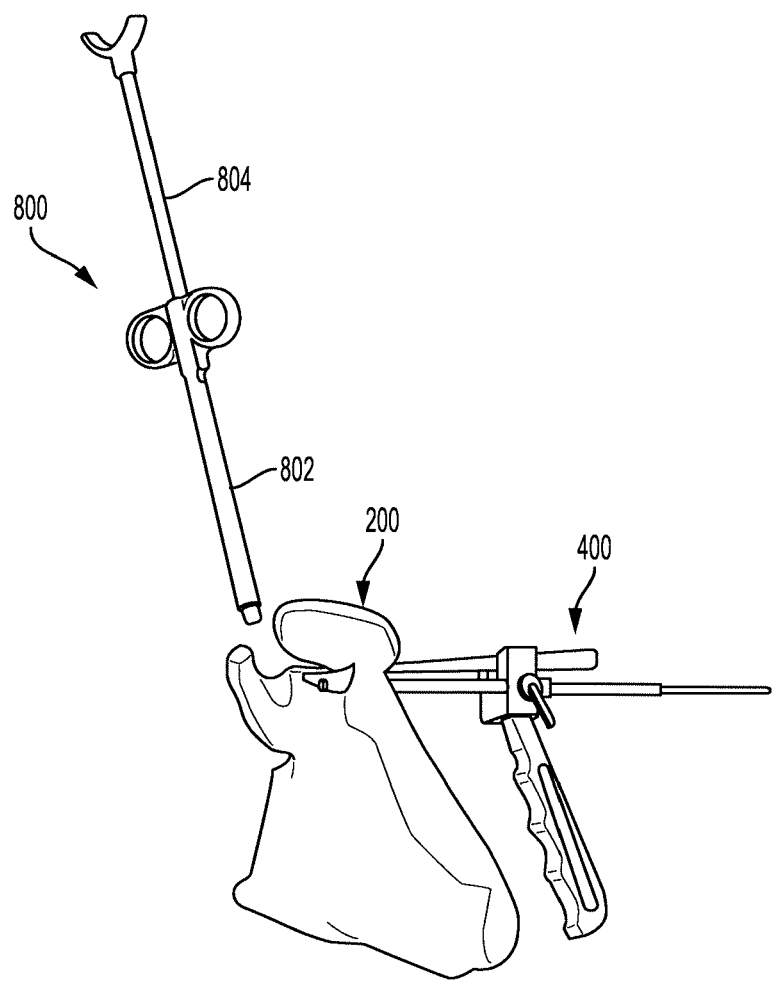
FIG. 8 is a perspective view of the expanding cannula system of FIG. 7 inserted through the rotator cuff interval of an embodiment.
Figure 9:
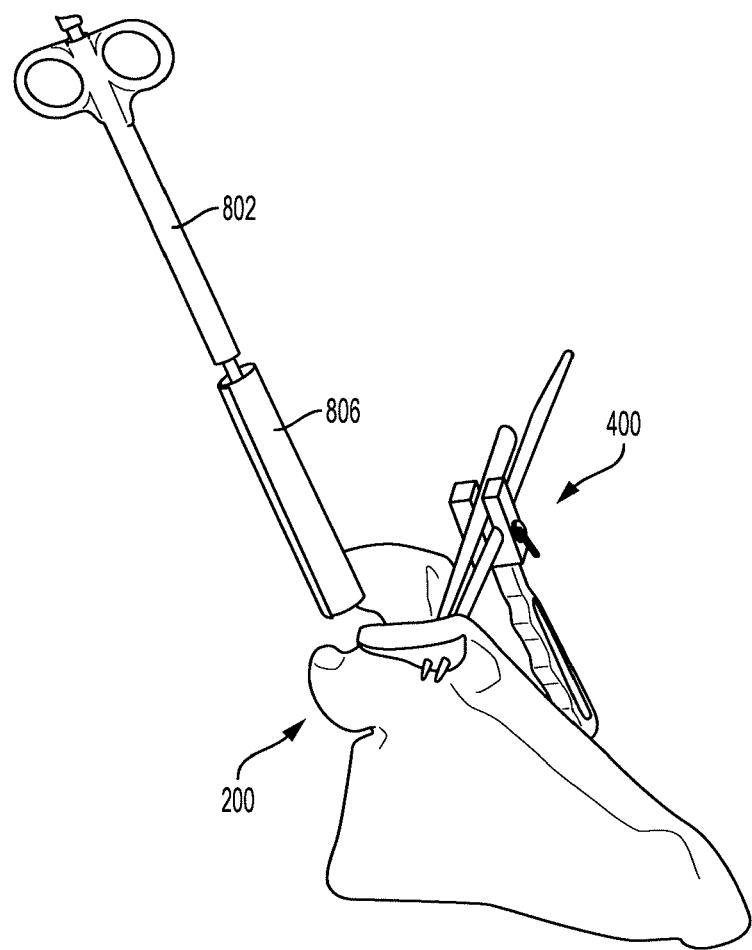
FIG. 9 is a perspective view of a roll of film deposited into the rotator cuff interval by the expanding cannula system of FIG. 7 of an embodiment.

As stated above and shown in FIG. 6, the bone block 100 is threaded onto the implant suture 700a, which is also threaded through the aperture 308 of the fastener 300. To facilitate implantation of the bone block 100, an expanding cannula system 800 can be used. The embodiment of the expanding cannula system 800 shown in FIG. 7 comprises an inserter 802 having a cannula 804 therein. The inserter 802 can be loaded with a roll of plastic film 806 or other similar material. Once the roll of plastic film 806 is placed within the inserter 802, the expanding cannula system 800 can be loaded into the rotator cuff interval, as shown in FIG. 8. In the embodiment shown in FIG. 8, the drill system 400 remains in place within the glenoid bone 200 while the expanding cannula system 800 is inserted through the rotator cuff interval. The expanding cannula system 800 is then deployed such that the roll of film 806 is unloaded into the rotator cuff interval, as shown in FIG. 9. Once the inserter 802 and the cannula 804 are removed, the roll of film 806 unravels slighting within the rotator cuff interval, forming a tube therein.

Figure 10:
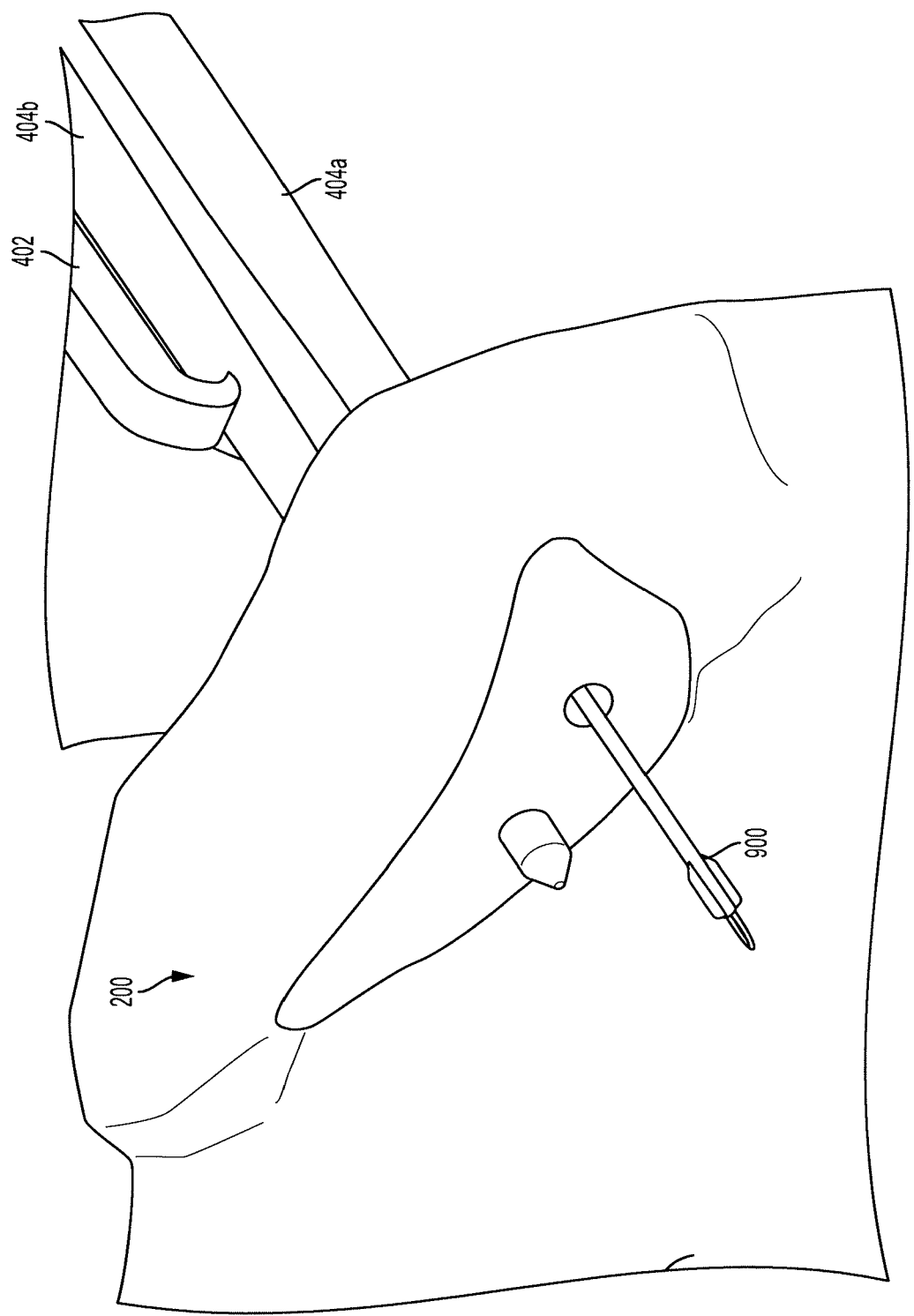
FIG. 10 is close-up view of an exemplary embodiment of a passing suture inserted through a bore in the glenoid bone via a drill guide.
Figure 11:
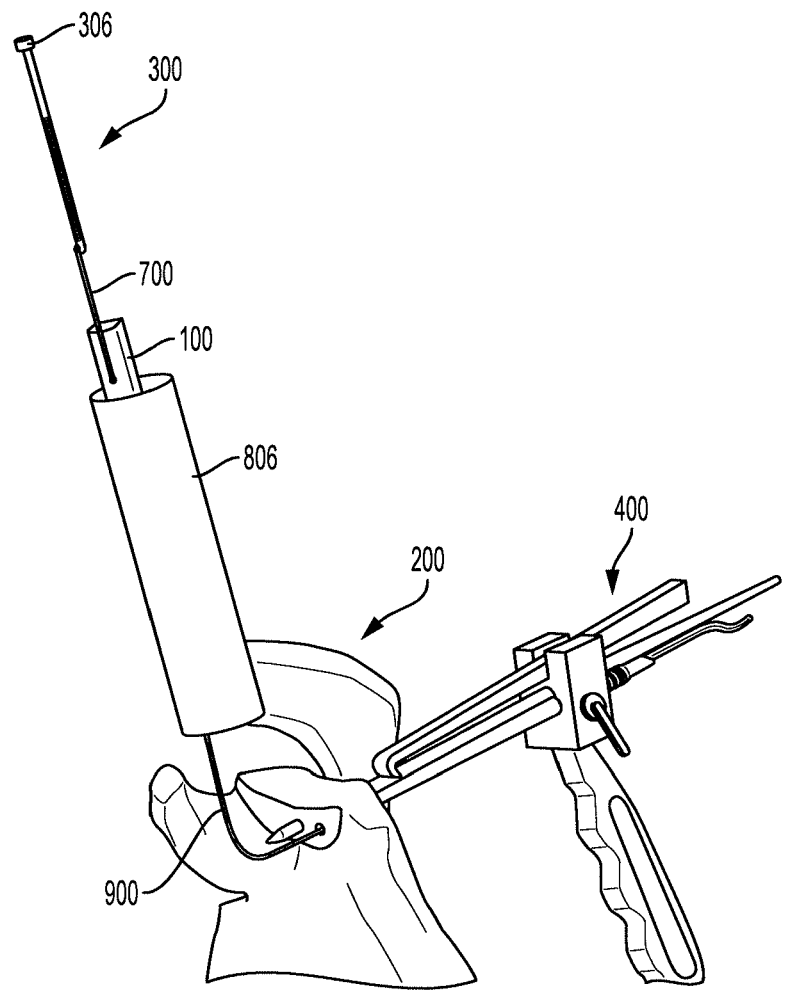
FIG. 11 is a perspective view of the connected implant suture, bone block, and fastener of FIG. 6 deposited into the roll of film of FIG. 9 of an embodiment.
Figure 12:
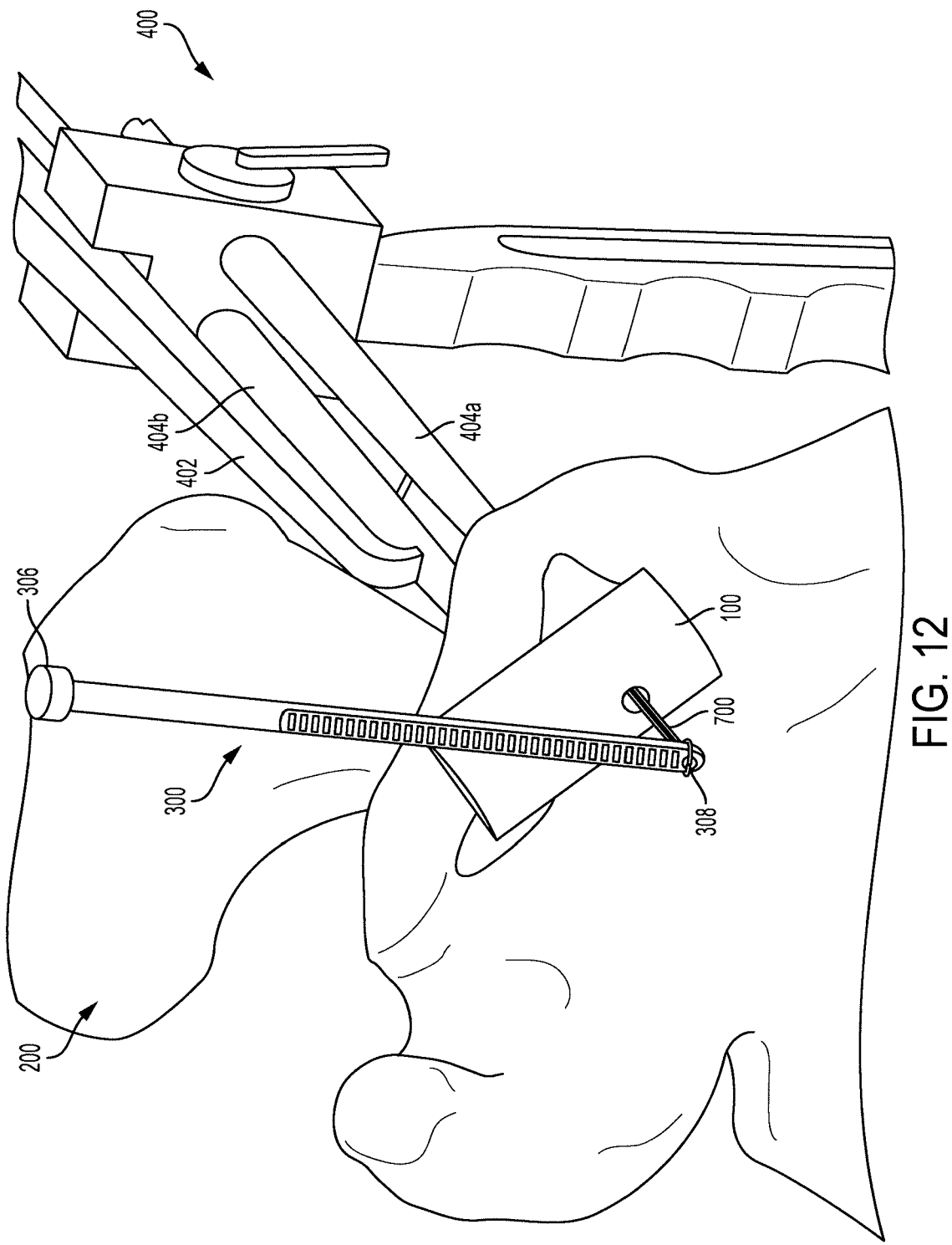
FIG. 12 is a close-up view the implant suture pulling the fastener through the bore in the bone block and the glenoid bone of an embodiment.
Figure 13:
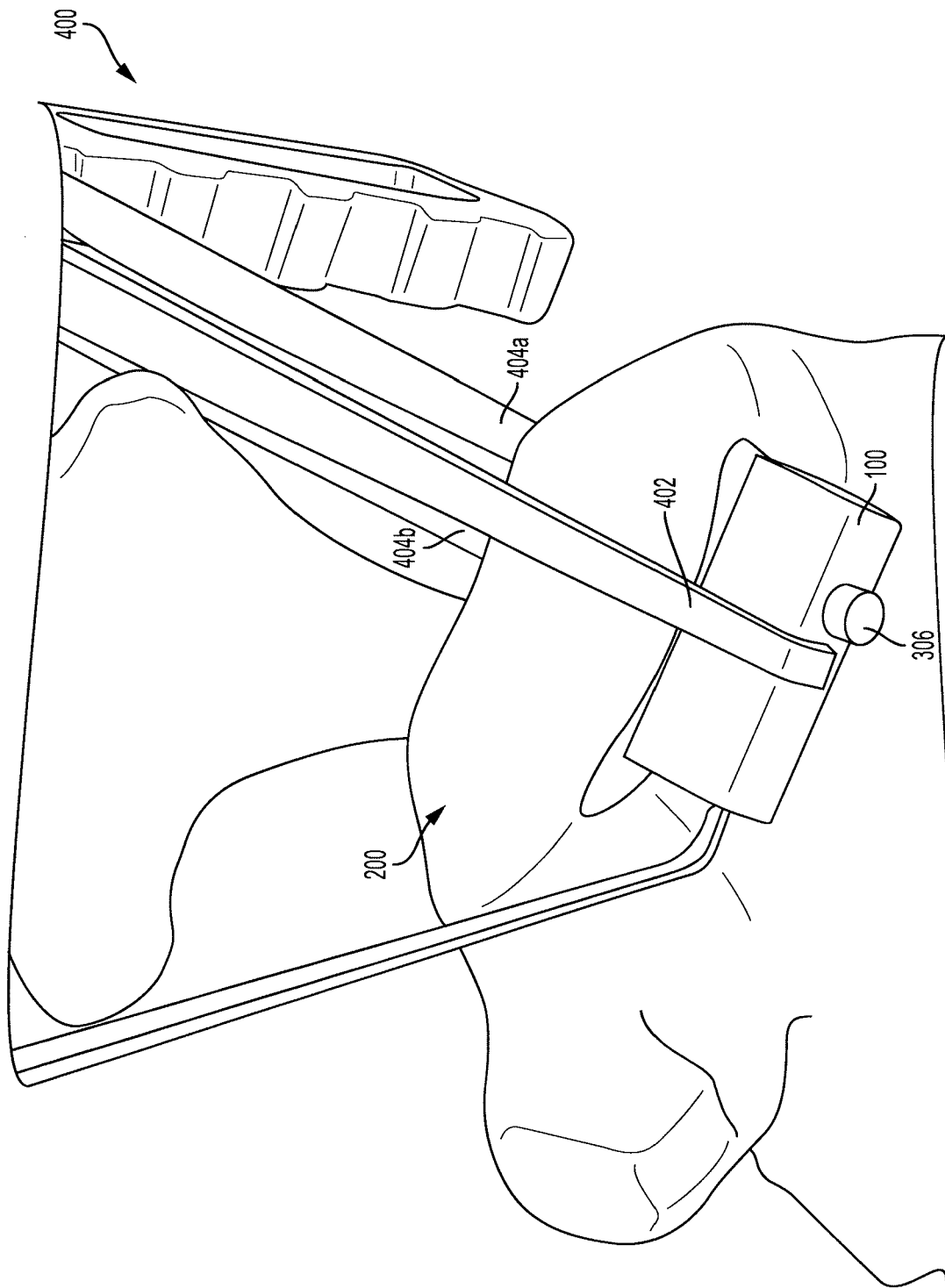
FIG. 13 is a close-up view of the fastener within the bore in the bone block and the glenoid bone of an embodiment.

Referring now to FIG. 10, at the next step, a passing suture 900 is inserted posteriorly via the inferior drill guide 404a through the inferior bore in the glenoid bone 200. An example of the tool used to insert the passing suture 900 is the Y-Knot® suture anchor driver made by ConMed® Corporation. The passing suture 900 can aid in pulling the bone block 100 in place against the glenoid bone 200. Referring now to FIGS. 11-13, there are shown perspective views of the implantation of the bone block 100 against the glenoid bone 200. As shown in FIG. 11, the implant suture 700 connected to the bone block 100 and first fastener 300a is inserted into the roll of film 806. The passing suture 900 is then used to retrieve the tails 702a of the implant suture 700a.

Grasping the tails 702a of the implant suture 700a, the passing suture 900 can be used to pull the bone block 100 and the attached first fastener 300a (which can be a zip tie, or suture attached to a button head 306a (made from a biocompatible material such as PEEK and/or PEG) down through the roll of film 806 to the glenoid bone 200, as shown in FIG. 12. Referring now to FIG. 13, the passing suture 900 and the implant suture 700 are pulled tightly until the bone block 100 is flush against the glenoid bone 200 and pivoted into position from the angled position (with respect to the glenoid bone 200) as shown in FIG. 12. In this position, the cord 302 of the first fastener 300a extends through the bore of the glenoid bone 200 such that the button 306a rests on the anterior side over the bore in the bone block 100. In the embodiments depicted in FIGS. 11-13, the first fastener 300a is composed of sturdy yet flexible material such that the cord 302 of the first fastener 300a can bend from a substantially vertical position to a substantially horizontal position when the first fastener 300a is pulled through the bores in the bone block 100 and the glenoid bone 200. An example of such material is polyetheretherketone (PEEK) and/or polyethylene glycol (PEG).

Figure 14:
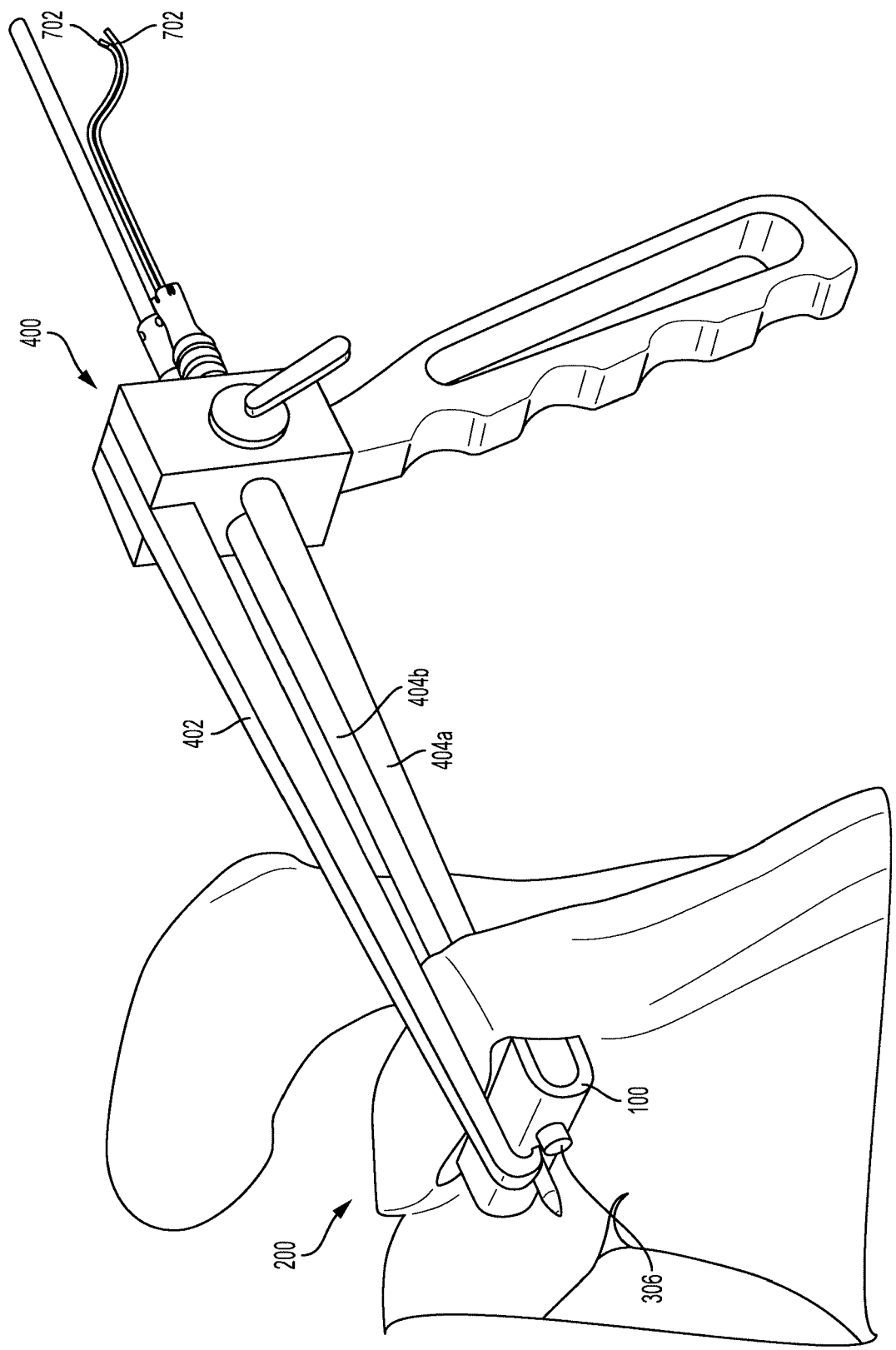
FIG. 14 is a side view of a second bore in the bone block created by the drill system of an embodiment.

Also shown in FIG. 13, with the bone block 100 held temporarily in position by tension on the passing suture 900, the hook 402 of the drill system 400 is employed again to hold the bone block 100 in place against the glenoid bone 200. Referring now to FIG. 14, the superior drill guide 404b is used to drill a superior second bore in the bone block 100. The superior bore in the glenoid bone 200 is extended to a superior, second bore in the bone block 100. This step of the procedure improves the alignment of the bores in the glenoid bone 200 and the bores in the bone block 100. Traditional methods of implanting a bone block require two bores drilled through the bone block prior to alignment along the glenoid bone. To achieve precise alignment in traditional methods, cautious and exact measurements are required. Even exercising the utmost caution, exact measurements may not translate well to the surgical setting wherein surrounding tissue, contours of the bone, and other ambient conditions may cause misalignment. In the embodiment shown in FIG. 14, there are no measurements required for making the second bore in the bone block 100.

Figure 15:
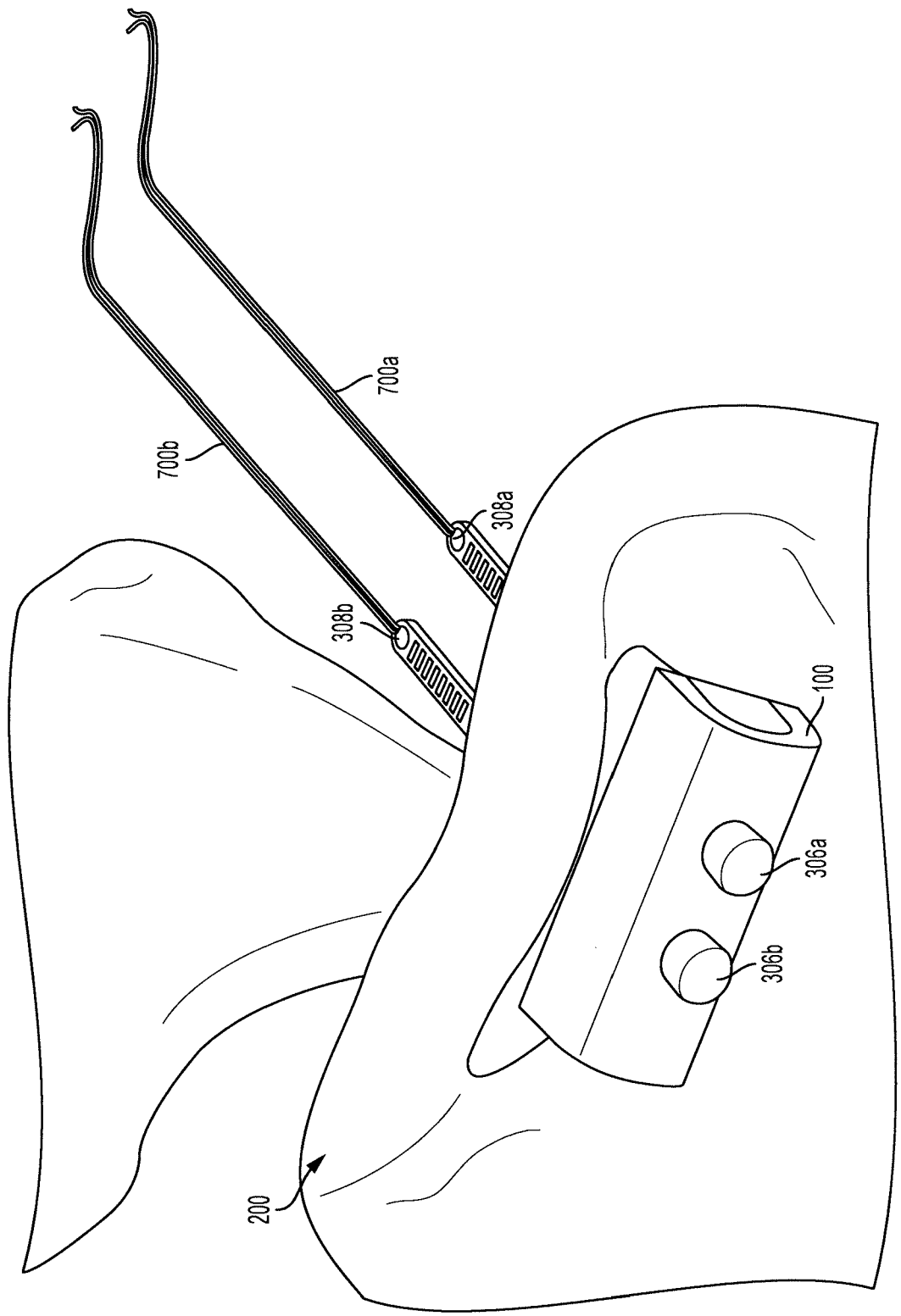
FIG. 15 is a close-up view of a first and a second fastener secure within the first and second bores of the bone block and glenoid bone of an embodiment.

After the superior, second bore is drilled through the bone block 100, a passing suture 900 can be extended therethrough to retrieve the tails 702b of a second implant suture 700b connected to a second fastener 300b. Similarly, as described above with respect to the first fastener 300a, the second fastener 300b is pulled through the second bore of both the bone block 100 and the glenoid bone 200 until the button 306b of the second fastener 300b rests against the bone block 100, following the steps shown in FIGS. 8-12. With tension on both sutures 700a,b holding the fasteners 300a,b in place, the drill hook 402 is detached and the drill guides 404 are removed, as shown in FIG. 15.

Figure 16:
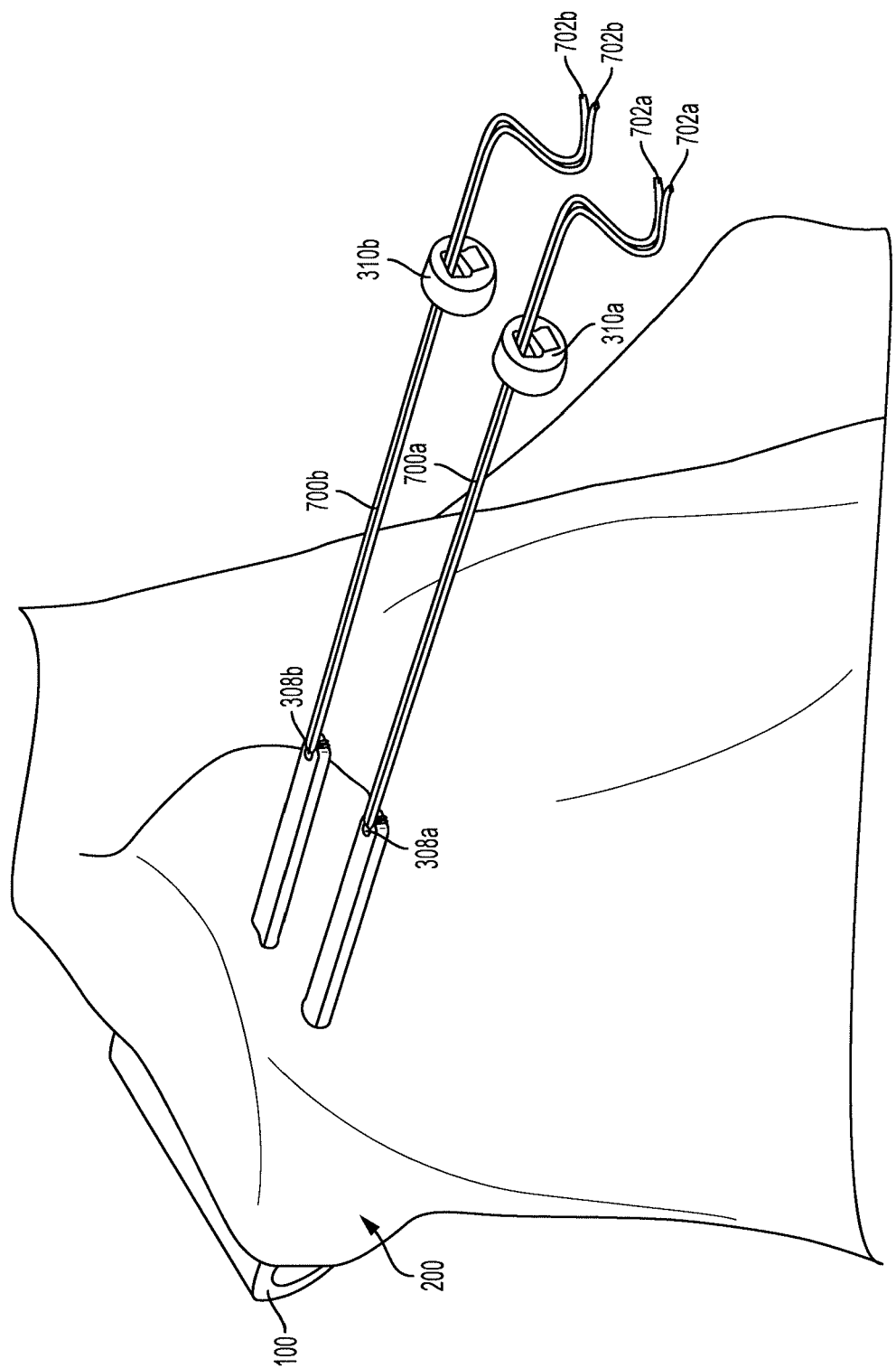
FIG. 16 is a rear view of the glenoid bone with an exemplary embodiment of tensioning locks shuttled along the implant sutures of an embodiment.

Referring now to FIG. 16, once the drill system 400 is removed, tensioning locks 310a,b are shuttled down respective implant sutures 700a,b to the free ends of the fasteners 300a,b. Respective cords 302 of fasteners 300a,b are fed through the tensioning locks 310a,b. The tensioning locks 310a,b can progress along the ratcheted sections 304 of the cords 302 wherein features of the tensioning locks 310a,b catch thereon. The farther the tensioning locks 310a,b move along the ratcheted sections 304 towards the respective buttons 306a,b of the fasteners 300a,b, the tighter the bone block 100 is held against the glenoid bone 200, thus securing the bone block 100 in position.

Figure 17:
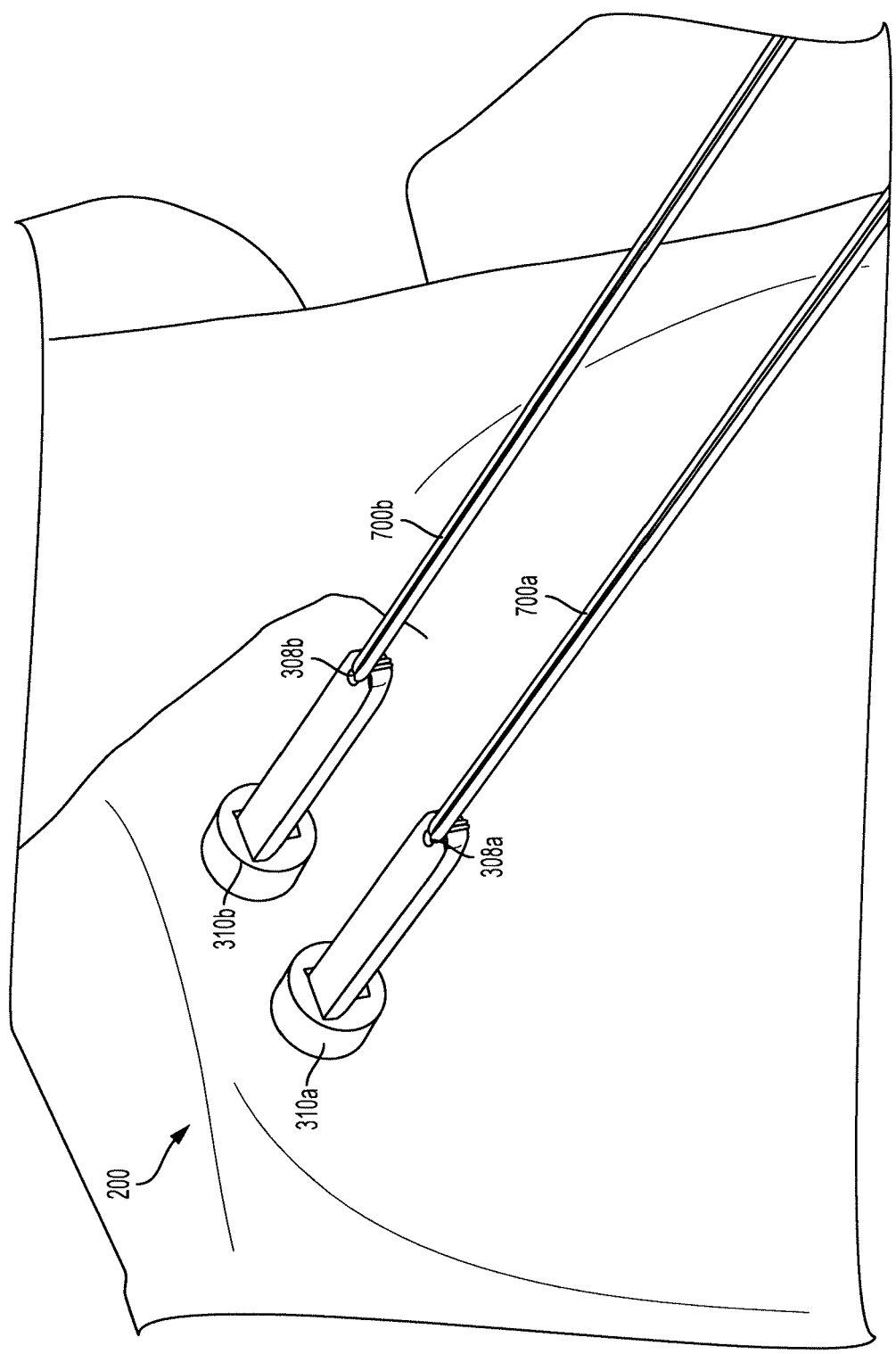
FIG. 17 is a rear close-up view of the tensioning locks secured to a cord of the fastener of an embodiment.
Figure 18:
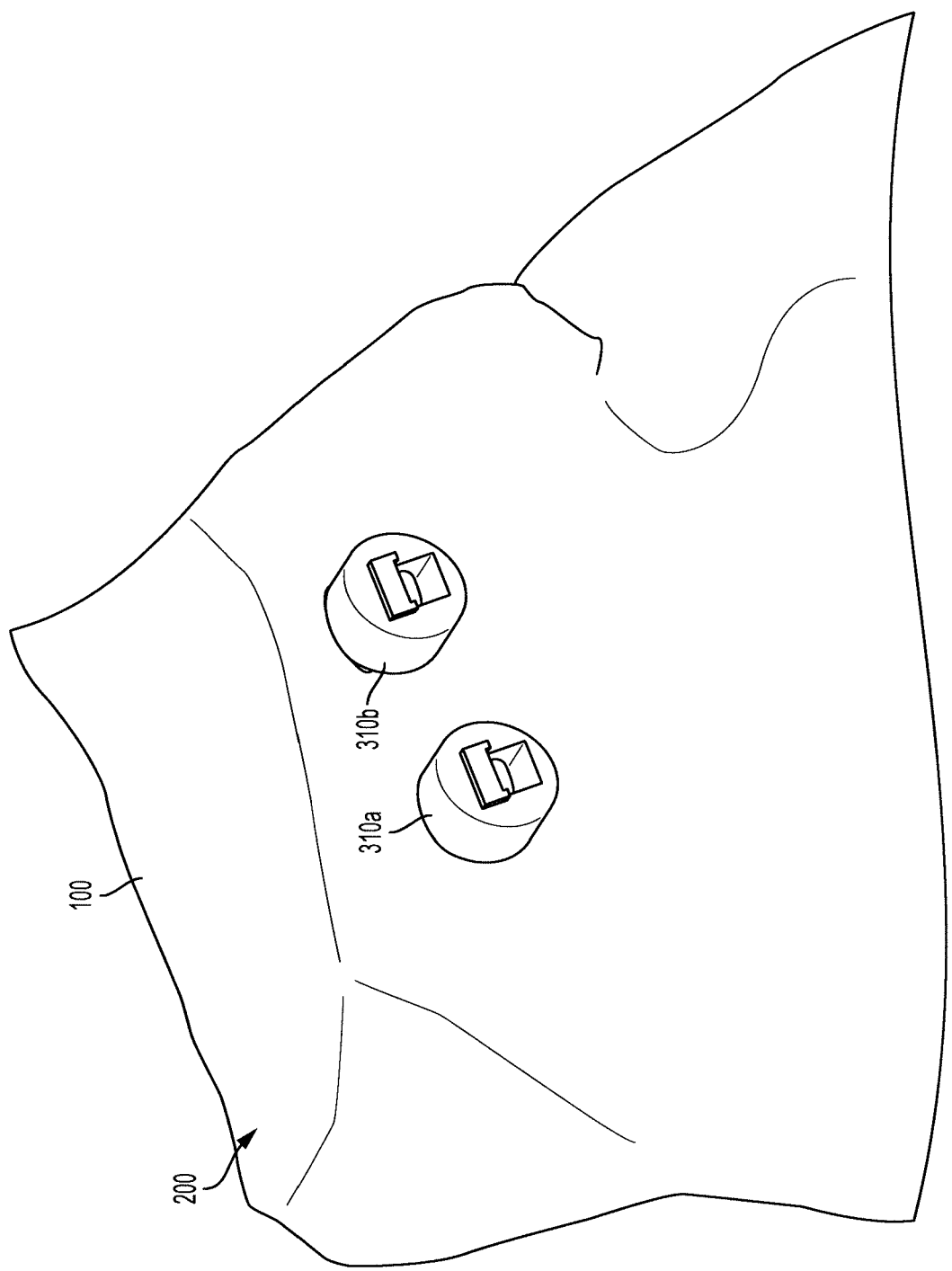
FIG. 18 is a rear close-up view of the tensioning locks with an excess portion of the cord removed of an embodiment.
Figure 19A:
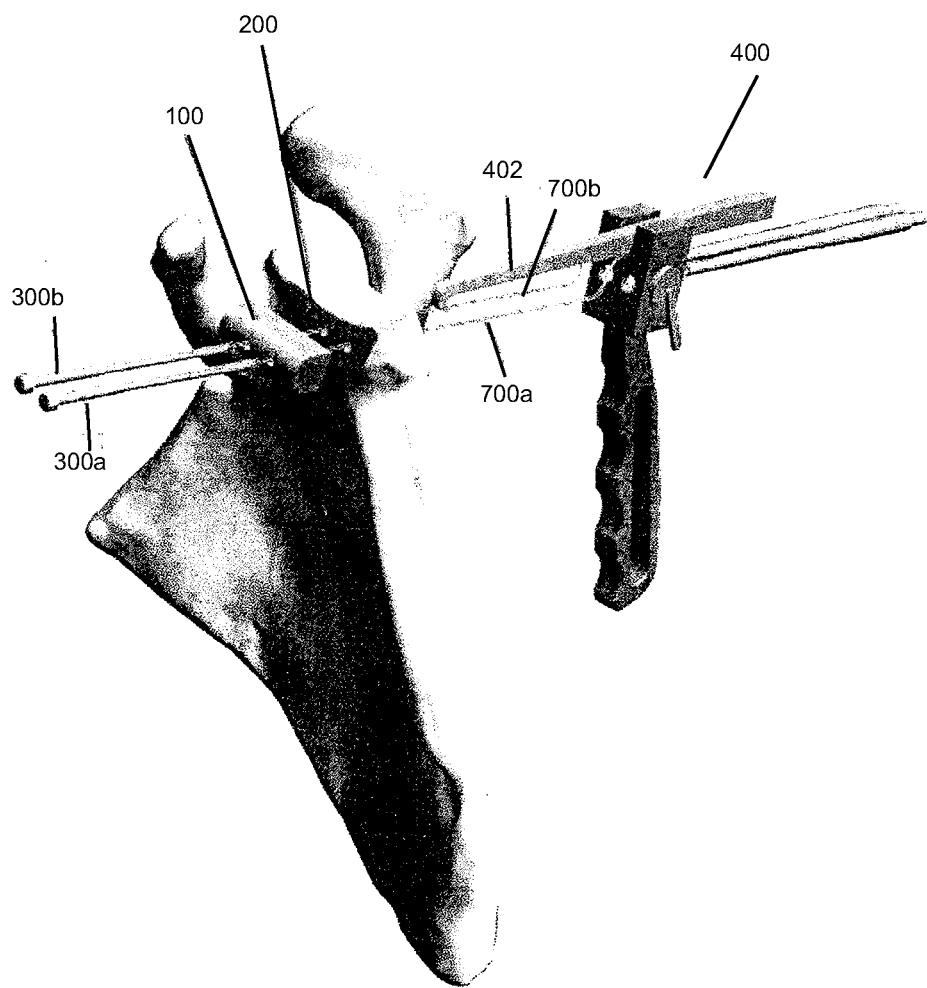
FIG. 19A is a perspective view of the drill assembly, bone block and fasteners in a semi exploded view to show many parts of the system together with reference to the glenoid bone of an embodiment.
Figure 19B:
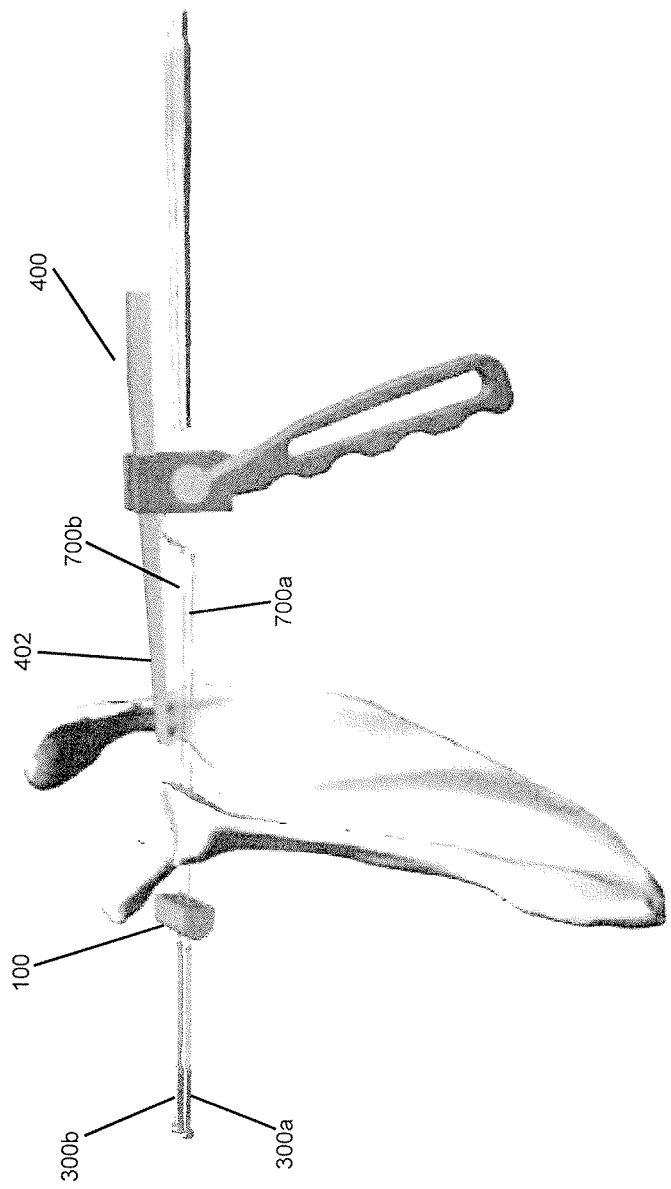
FIG. 19B is a perspective view of the drill assembly, bone block and fasteners in a semi exploded view to show many parts of the system together with reference to the glenoid bone.
Figure 20B:
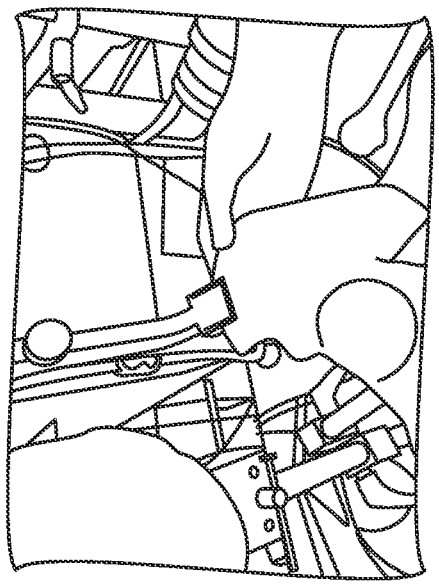
FIG. 20B is a picture showing part of a method of harvesting and preparing a bone block graft of an embodiment.
Figure 20D:
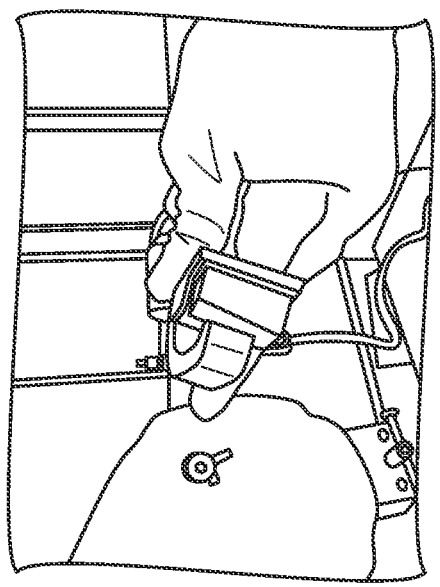
FIG. 20D is a picture showing part of a method of harvesting and preparing a bone block graft of an embodiment.
Figure 20A:
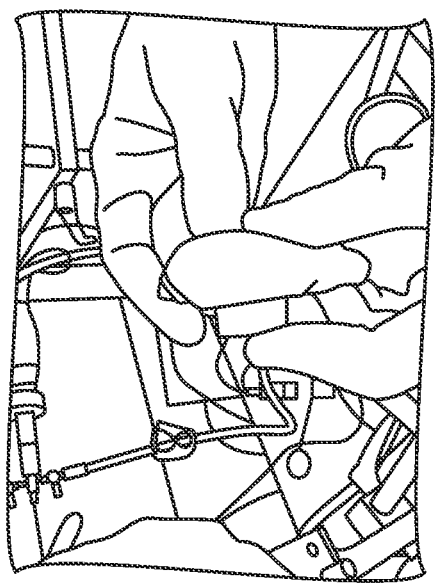
FIG. 20A is a picture showing part of a method of harvesting and preparing a bone block graft of an embodiment.
Figure 20C:
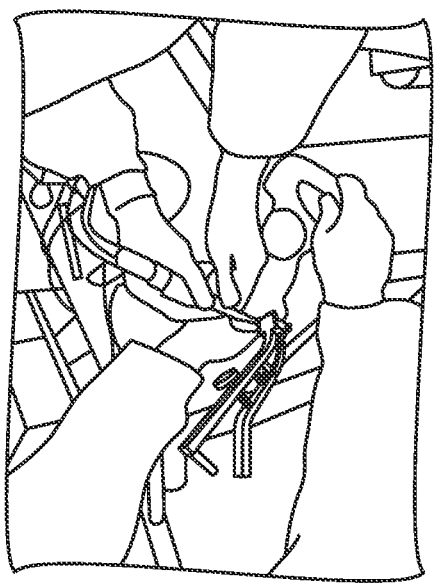
FIG. 20C is a picture showing part of a method of harvesting and preparing a bone block graft of an embodiment.
Figure 21A:
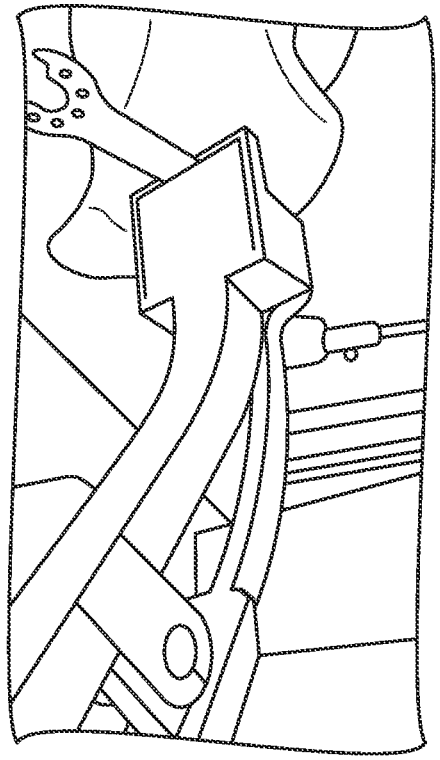
FIG. 21A is a picture showing part of a method of harvesting and preparing a bone block graft of an embodiment.
Figure 21B:
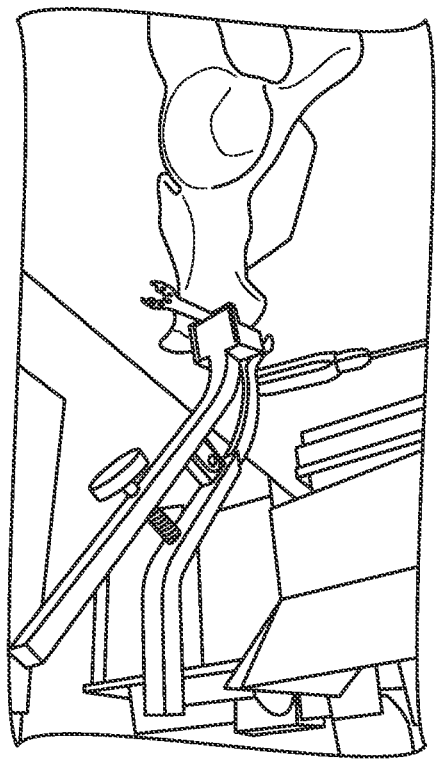
FIG. 21B is a picture showing part of a method of harvesting and preparing a bone block graft of an embodiment.
Figure 21C:
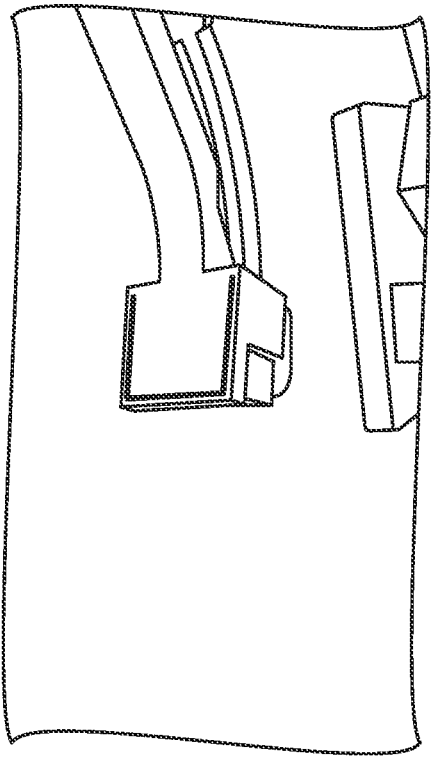
FIG. 21C is a picture showing part of a method of harvesting and preparing a bone block graft of an embodiment.
Figure 21D:
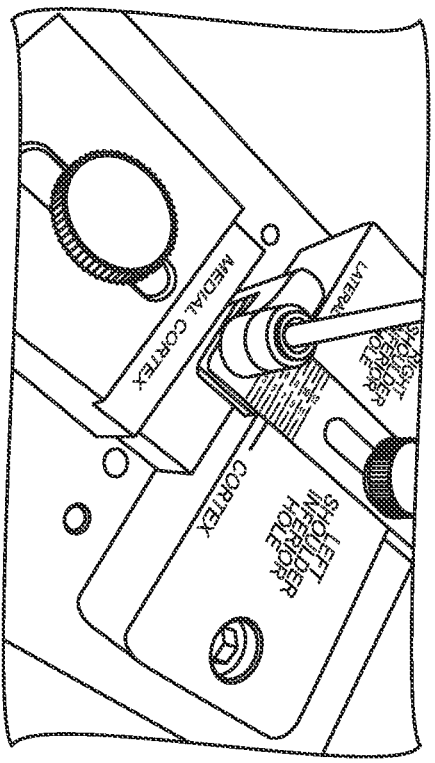
FIG. 21D is a picture showing part of a method of harvesting and preparing a bone block graft of an embodiment.
Figure 21F:
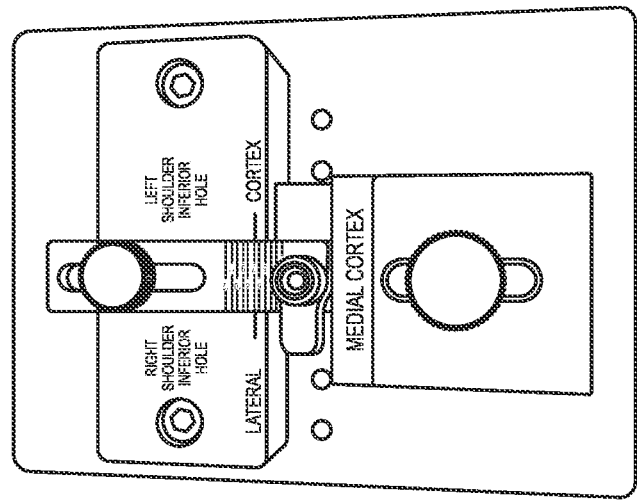
FIG. 21F is a picture showing part of a method of harvesting and preparing a bone block graft of an embodiment.
Figure 21E:
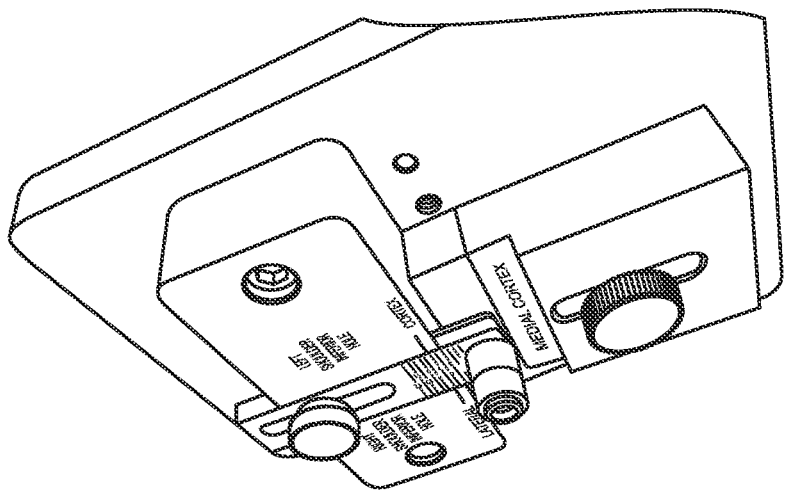
FIG. 21E is a picture showing part of a method of harvesting and preparing a bone block graft of an embodiment.

The tensioning locks 310a,b can be threaded farther down the ratcheted sections 304 until the desired force holding the bone block 100 against the glenoid bone 200 is achieved. Thus, as shown in the embodiment depicted in FIG. 17, the buttons 306a,b surround the bores on the anterior side of the bone block 100, while the tensioning locks 310a,b surround the bores on the posterior side of the glenoid bone 200. In the embodiment shown in FIG. 17, excess portions of the cords 302 extend from the posterior of the tensioning locks 310a,b. These portions can be excised so that the cords 302 secured within the tensioning locks 310a,b are flush with the tensioning locks 310a,b, as shown in FIG. 18. This ensures that there is not excess material surrounding the glenoid bone 200 that could cause additional trauma, discomfort, and increased recovery time.

An embodiment of a method of harvesting and preparing a bone block graft 100 is described below in conjunction with FIGS. 20A-D (showing harvesting a bone graft)-21A-D (showing the making and measuring of a bone block).

A graft harvesting tool (as should be understood by those of ordinary skill in the art in conjunction with a review of this disclosure) is positioned and secured by attaching a clamping mechanism onto a patient's iliac crest for an autograft or a donor iliac crest bone portion in the case of an allograft. An allograft distal tibia could be used as the graft but this may require a different cutting jig. It could consist of a clamp designed to hold the distal tibia donor bone portion and two cutting fences similar to the meniscal transplant system described, for example, in U.S. Ser. No. 10/034,778.

An accurately shaped and sized cuboid shaped graft may then be cut from the patient or donor bone portion by following the cutting guide slots integrated into the harvesting tool with an oscillating sagittal saw. The graft produced can typically be 10 mm high by 25 mm long with a thickness equal to that of the original iliac crest. In other words, three sides of the cuboid shaped graft are cut with the sagittal saw i.e. the two ends and one long side while the remaining three surfaces are untouched native cortex. The graft can then be removed from the harvesting tool. The graft's concave lateral cortical surface is marked with a surgical pen to ensure it will be correctly oriented with the concave lateral face of the glenoid.

The graft drilling jig (as further shown in and described with respect to FIG. 5, above) can incorporate an adjustable end stop which may be positioned to accommodate drilling of the graft for a left or right shoulder repair procedure by rotating the stop to the left hand or right hand side of the sliding scale. The end stop pivot point is attached to the proximal end of a sliding scale which is marked with graduated measuring indicia. The scale may slide linearly in a slot formed into a fixed block rigidly attached to a base plate. The scale may be locked at a desired position per the measurement indicia. The drilling jig can also feature an opposing block which can slide linearly and may be locked in position to secure the graft during drilling. The drilling jig may be laser marked "LEFT" and "RIGHT" (or similar) to clearly indicate the required side to set the end stop and also the fixed block may be laser marked "LATERAL/CONCAVE" to assist in correct orientation of the previously marked lateral/concave surface of the graft. The center of the pivot point of the end stop can have a coaxial through-hole which forms a drill bushing to control the drilling of a hole through the graft at a predetermined distance from its concave surface as set by the adjustable scale and also at a predetermined fixed offset from the end of the graft as set by the adjustable end stop. The drill may include a stop collar at a predetermined distance from the drill tip. This distance could be preset to match a corresponding dimension of the drill bushing to control the correct depth that the drill must travel to fully penetrate the graft.

After the correct adjustments have been made to the drilling jig described above, a single primary hole can be drilled through the graft. The markings on the jig would be arranged to guide the user to drill the primary hole in the inferior end of the graft in order to improve the anteroinferior visualization of the graft during later steps in the procedure. The graft now awaits preparation of the glenoid as described further below.

While various embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as, "has" and "having"), "include" (and any form of include, such as "includes" and "including"), and "contain" (any form of contain, such as "contains" and "containing") are open-ended linking verbs. As a result, a method or device that "comprises", "has", "includes" or "contains" one or more steps or elements. Likewise, a step of method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

The corresponding structures, materials, acts and equivalents of all means or step plus function elements in the claims below, if any, are intended to include any structure, material or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the present invention for various embodiments with various modifications as are suited to the particular use contemplated.

What is claimed is:

1. A method of securing a bone graft to an anterior surface of a patient's glenoid bone, comprising the steps of:
    drilling a first bore through a first portion of a posterior surface to a first portion of an anterior surface of the glenoid bone;
    drilling a second bore through a second portion of the posterior surface to a second portion of the anterior surface of the glenoid bone;
    measuring a medial distance of the first bore;
    transferring the medial distance to a bone block;
    drilling a third bore based on the medial distance through a first surface to a second surface, or through a second surface to a first surface, of the bone block to match the first bore;
    positioning a first portion of the first surface of the bone block in contacting relation with the first portion of the anterior surface of the glenoid bone, and coaxially lining up the third bore of the bone block with the first bore of the glenoid bone;
    positioning a first fastener through the third bore and the first bore;
    positioning a second portion of the first surface of the bone block in contacting relation with the second portion of the anterior surface of the glenoid bone;

drilling a fourth bore in the bone block by positioning a drill bit through the second bore from the posterior side of the glenoid bone, and extending the drill bit from a second portion of the first surface of the bone block to the second surface of the bone block; and positioning a second fastener through the fourth bore and the second bore.

2. The method of claim 1, further comprising the step of removing soft tissue from the anterior surface of the glenoid bone.

3. The method of claim 2, further comprising the step of smoothing and flattening the anterior surface of the glenoid bone.

4. The method of claim 1, wherein the first bore and the second bore are drilled simultaneously.

5. The method of claim 4, wherein the first bore is an inferior bore and the second bore is a superior bore.

6. The method of claim 5, wherein the step of measuring a medial distance of the first bore comprises measuring the medial distance of an exit point of the first bore on the anterior side of the glenoid bone when an inferior drill bit positioned therethrough.

7. The method of claim 1, further comprising the step of threading an implant suture through an aperture in the first fastener and pulling the implant suture through the third bore of bone block from the second surface to the first surface of the bone block.

8. The method of claim 7, further comprising the step of inserting a passing suture through the first bore from the posterior side of the glenoid bone to the anterior side of the glenoid bone.

9. The method of claim 8, further comprising the step of implanting the bone block into the patient through an expanding cannula system comprising a roll of film.

10. The method of claim 9, further comprising the step of grasping a portion of the implant suture by the passing suture and pulling the bone block and the attached fastener through the roll of film so that the first surface of the bone block is in contacting relation to the anterior surface of the glenoid bone and the first fastener is positioned through the third bore and the first bore.

11. The method of claim 10, wherein the first fastener comprises a cord with a free end and a button affixed to an opposing end with a ratcheted section therebetween, wherein the cord extends through the first bore such that the button rests on the second surface of the bone block and the free end extends posteriorly through and beyond the third bore and the first bore after the step of positioning the first fastener through the third bore and the first bore.

12. The method of claim 11, further comprising the step of positioning a tensioning lock onto the free end of the cord anteriorly towards the button, wherein in a locked position, the tensioning lock is affixed to the ratcheted section.

13. The method of claim 1, further comprising the step of securing the bone block to the anterior surface of the glenoid bone after the step of positioning the second portion of the first surface of the bone block in contacting relation with the second portion of the anterior surface of the glenoid bone.

14. The method of claim 13, wherein the step of securing comprises the step of extending a hook of a drill system in contacting relation to the second surface of the bone block and applying a force against the second surface of the bone block.

15. The method of claim 1, further comprising the step of threading an implant suture through an aperture in the second fastener.

16. The method of claim 15, further comprising the step of inserting a passing suture through the second bore and the fourth bore from the posterior side of the glenoid bone to the second side of the bone block.

17. The method of claim 16, further comprising the step of grasping a portion of the implant suture by the passing suture and pulling the attached fastener so that the first fastener is positioned through the fourth bore and the second bore.

18. The method of claim 17, wherein the second fastener comprises a cord with a free end and a button affixed to an opposing end with a ratcheted section therebetween, wherein the cord extends through the second bore such that the button rests on the second surface of the bone block and the free end extends posteriorly through and beyond the fourth bore and the second bore after the step of positioning the second fastener through the fourth bore and the second bore.

19. The method of claim 18, further comprising the step of positioning a tensioning lock onto the free end of the cord anteriorly towards the button, wherein in a locked position, the tensioning lock is affixed to the ratcheted section.

* * * * *